US009955966B2

(12) United States Patent
Zergiebel

(10) Patent No.: US 9,955,966 B2
(45) Date of Patent: May 1, 2018

(54) ADAPTER DIRECT DRIVE WITH MANUAL RETRACTION, LOCKOUT, AND CONNECTION MECHANISMS FOR IMPROPER USE PREVENTION

(71) Applicant: Covidien LP, Mansfield, MA (US)

(72) Inventor: Earl M. Zergiebel, Guilford, CT (US)

(73) Assignee: Covidien LP, Mansfield, MA (US)

(*) Notice: Subject to any disclaimer, the term of this patent is extended or adjusted under 35 U.S.C. 154(b) by 503 days.

(21) Appl. No.: 14/307,992

(22) Filed: Jun. 18, 2014

(65) Prior Publication Data
US 2015/0076205 A1    Mar. 19, 2015

Related U.S. Application Data

(60) Provisional application No. 61/878,934, filed on Sep. 17, 2013.

(51) Int. Cl.
*A61B 17/04* (2006.01)
*A61B 17/10* (2006.01)
(Continued)

(52) U.S. Cl.
CPC ...... *A61B 17/068* (2013.01); *A61B 17/07207* (2013.01); *A61B 17/320016* (2013.01);
(Continued)

(58) Field of Classification Search
CPC ........ A61B 17/068; A61B 2017/00477; A61B 2017/07278; A61B 2017/292; A61B 2017/294; A61B 2017/320016
(Continued)

(56) References Cited

U.S. PATENT DOCUMENTS 2,777,340 A   1/1957   Hettwer et al.
2,957,353 A   10/1960  Babacz
(Continued)

FOREIGN PATENT DOCUMENTS

AU   2008229795 A1   4/2009
CA      2451558 A1   1/2003
(Continued)

OTHER PUBLICATIONS

European Examination Report for Application No. 14 184 882.0 dated Apr. 25, 2016.
(Continued)

*Primary Examiner* — Robert Long

(57) ABSTRACT

A surgical device adapter for coupling an end effector to a handle assembly is provided. The surgical device adapter includes a housing and a drive mechanism disposed within the housing and couplable to the handle assembly and the end effector. The surgical device adapter also includes a drive coupling assembly coupled to the surgical device adapter and selectively couplable to the handle assembly. The drive coupling assembly includes retraction assembly movable from a first configuration to a second configuration, wherein in the first configuration the retraction assembly is disengaged from the drive mechanism and in the second configuration the retraction assembly is engaged with the drive mechanism and prevents coupling of the handle assembly to the surgical device adapter.

14 Claims, 27 Drawing Sheets

(51) Int. Cl.
*A61B 17/068* (2006.01)
*A61B 17/072* (2006.01)
*A61B 17/32* (2006.01)
*A61B 17/00* (2006.01)
*A61B 17/29* (2006.01)

(52) U.S. Cl.
CPC ............ *A61B 2017/0046* (2013.01); *A61B 2017/00477* (2013.01); *A61B 2017/2931* (2013.01)

(58) Field of Classification Search
USPC .......................................... 227/175.1–182.1
See application file for complete search history.

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,033,552 A * | 7/1991 | Hu .................. B25B 21/00 173/170 |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |

(56) References Cited

U.S. PATENT DOCUMENTS

| | | |
|---|---|---|
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,402,604 B2 * | 8/2016 | Williams ......... A61B 17/07207 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0100867 A1 * | 5/2005 | Hilscher ............... A46B 5/0095 433/216 |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |

(56) References Cited

U.S. PATENT DOCUMENTS

| | | |
|---|---|---|
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0281336 A1* | 11/2008 | Zergiebel ............. A61B 17/068 606/142 |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0032179 A1* | 2/2010 | Hanspers ................ B25F 5/00 173/11 |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0022032 A1* | 1/2011 | Zemlok ............ A61B 17/07207 606/1 |
| 2011/0062211 A1* | 3/2011 | Ross ................ A61B 17/07207 227/175.1 |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0332243 A1* | 11/2014 | Baskar ..................... B25F 5/02 173/29 |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0343583 A1* | 12/2015 | McRoberts ............ B23Q 5/045 173/213 |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2016/0242779 A1* | 8/2016 | Aranyi ............. A61B 17/07207 |
| 2016/0270835 A1* | 9/2016 | Reed ................ A61B 17/00234 |

FOREIGN PATENT DOCUMENTS

| | | |
|---|---|---|
| CN | 101856251 A | 10/2010 |
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1 813 203 A2 | 8/2007 |
| EP | 1813199 A1 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 A1 | 7/2008 |
| EP | 1943976 A2 | 7/2008 |

(56) References Cited

FOREIGN PATENT DOCUMENTS

| | | |
|---|---|---|
| EP | 1952769 A2 | 8/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2090247 A1 | 8/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2815705 A1 | 12/2014 |
| EP | 2848204 A2 | 3/2015 |
| ES | 2333509 A1 | 2/2010 |
| FR | 2861574 A1 | 5/2005 |
| JP | 08-038488 | 2/1996 |
| JP | 2005-125075 A | 5/2005 |
| KR | 20120022521 A | 3/2012 |
| WO | 99/15086 A1 | 4/1999 |
| WO | 2000/072760 A1 | 12/2000 |
| WO | 2000/072765 A1 | 12/2000 |
| WO | 2003/000138 A2 | 1/2003 |
| WO | 2003/026511 A1 | 4/2003 |
| WO | 2003/030743 A2 | 4/2003 |
| WO | 2003065916 A1 | 8/2003 |
| WO | 2003/077769 A1 | 9/2003 |
| WO | 2003090630 A2 | 11/2003 |
| WO | 2004/107989 A1 | 12/2004 |
| WO | 2006/042210 A2 | 4/2006 |
| WO | 2007016290 A2 | 2/2007 |
| WO | 2007/026354 A1 | 3/2007 |
| WO | 2007137304 A2 | 11/2007 |
| WO | 2008/131362 A2 | 10/2008 |
| WO | 2008/133956 A2 | 11/2008 |
| WO | 2009039506 A1 | 3/2009 |
| WO | 2007014355 A3 | 4/2009 |
| WO | 2009/132359 A2 | 10/2009 |
| WO | 2009/143092 A1 | 11/2009 |
| WO | 2009149234 A1 | 12/2009 |
| WO | 2011/108840 A2 | 9/2011 |
| WO | 2012040984 A1 | 4/2012 |

OTHER PUBLICATIONS

European Search Report No. 14184882.0 dated Jan. 27, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
International Search Report corresponding to PCT/US2005/027266, completed May 30, 2008 and dated Jun. 18, 2008; (2 pp.).
Extended European Search Report corresponding to EP 08 25 2703.7, completed Oct. 23, 2008 and dated Oct. 31, 2008; (7 pp.).
Extended European Search Report corresponding to EP 08 25 3184.9, completed Feb. 12, 2009 and dated Feb. 27, 2009; (3 pp.).
Extended European Search Report corresponding to EP 10 25 0228.3, completed May 20, 2010 and dated Jun. 1, 2010; (6 pp.).
Extended European Search Report corresponding to EP 10 25 2037.6, completed Mar. 1, 2011 and dated Mar. 9, 2011; (3 pp.).
Extended European Search Report corresponding to EP 10 25 1968.3, completed on Jul. 4, 2011 and dated Jul. 14, 2011; (12 pp.).
Extended European Search Report corresponding to EP 11 15 2266.0, completed Jul. 15, 2011 and dated Jul. 28, 2011; (3 pp.).
Extended European Search Report corresponding to EP 11 25 0462.6, completed Jul. 20, 2011 and dated Jul. 28, 2011; (6 pp.).
Extended European Search Report corresponding to EP 11 25 0771.0, completed Feb. 7, 2012 and dated Feb. 17, 2012; (3 pp.).
Extended European Search Report corresponding to EP 06 78 8914.7, completed May 3, 2012 and dated May 11, 2012; (8 pp.).
Partial European Search Report corresponding to EP 12 18 6177.7, completed Jan. 30, 2013 and dated Feb. 12, 2013; (6 pp.).
Extended European Search Report corresponding to EP No. 11 17 8021.9, dated Jun. 4, 2013; (3 pp).
Extended European Search Report corresponding to EP No. 13 16 3033.7, completed Jun. 27, 2013 and dated Jul. 15, 2013; (8 pp).
Extended European Search Report corresponding to EP No. 12 18 6177.7, completed Aug. 14, 2013 and dated Aug. 23, 2013; (8 pp).
Partial European Search Report corresponding to EP No. 13 17 1742.3, completed Sep. 17, 2013 and dated Sep. 25, 2013; (8 pp).
Partial European Search Report corresponding to EP No. 13 17 2400.7, completed Sep. 18, 2013 and dated Oct. 1, 2013; (7 pp).
Extended European Search Report corresponding to EP No. 13 17 5475.6, completed Sep. 23, 2013 and dated Oct. 1, 2013; (8 pp).
Extended European Search Report corresponding to EP No. 13 17 5478.0, completed Sep. 24, 2013 and dated Oct. 2, 2013; (6 pp).

(56) References Cited

OTHER PUBLICATIONS

Extended European Search Report corresponding to EP No. 13 17 5479.8, completed Sep. 27, 2013 and dated Oct. 10, 2013; (7 pp).
Partial Extended European Search Report corresponding to EP 13 17 5477.2, completed Oct. 7, 2013 and dated Oct. 15, 2013; (7 pp).
Extended European Search Report corresponding to EP No. 08 25 2703.7, completed Oct. 23, 2008 and dated Oct. 31, 2008; (7 pp).
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
The extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
Extended European Search Report corresponding to Application No. EP 14152236.7 dated May 12, 2014.
Partial European Search Report from Application No. EP 14159056.2 dated Jun. 18, 2014 (8 pp).
European Examination Report from Appl. No. EP 14 184 882.0 dated Jan. 30, 2017.
Chinese Office Action dated Nov. 29, 2017 issued in corresponding Chinese Appln. No. 201410475358X. (English translation and Summary only).

\* cited by examiner

ADAPTER DIRECT DRIVE WITH MANUAL RETRACTION, LOCKOUT, AND CONNECTION MECHANISMS FOR IMPROPER USE PREVENTION

CROSS-REFERENCE TO RELATED APPLICATIONS

This application claims the benefit of and priority to U.S. Provisional Patent Application No. 61/878,934, filed Sep. 17, 2013, the entire disclosure of which is incorporated by reference herein.

BACKGROUND

1. Technical Field

The present disclosure relates to surgical apparatuses, devices and/or systems for performing endoscopic surgical procedures and methods of use thereof. More specifically, the present disclosure relates to electromechanical, hand-held surgical apparatuses, adapters, devices and/or systems configured for use with removable disposable loading units and/or single use loading units for clamping, cutting and/or stapling tissue.

2. Background of Related Art

Currently there are various drive systems for operating and/or manipulating electromechanical surgical devices. In many instances the electromechanical surgical devices include a reusable handle assembly, and disposable or single-use loading units. The loading units are selectively connected to the handle assembly prior to use and then disconnected from the handle assembly following use in order to be disposed of or in some instances sterilized for re-use.

Many of the existing end effectors for use with many of the existing surgical devices and/or handle assemblies are driven by a linear force. For example, end effectors for performing endo-gastrointestinal anastomosis procedures, end-to-end anastomosis procedures and transverse anastomosis procedures, each typically require a linear driving force in order to be operated. As such, these end effectors are not compatible with surgical devices and/or handle assemblies that use rotary motion to deliver power or the like.

In order to make the linear driven end effectors compatible with surgical devices and/or handle assemblies that use a rotary motion to deliver power, a need exists for adapters and/or adapter assemblies to interface between and interconnect the linear driven end effectors with the rotary driven surgical devices and/or handle assemblies. There is also a need for adapters that include manual retraction, connection, and locking and release mechanisms for coupling to the surgical devices. There is additional need for mechanisms to prevent accidental actuation of manual retraction mechanisms.

SUMMARY

Further details and aspects of exemplary embodiments of the present invention are described in more detail below with reference to the appended Figures.

According to one embodiment of the present disclosure, a surgical device adapter for coupling an end effector to a handle assembly is provided. The surgical device adapter includes a housing and a drive mechanism disposed within the housing and couplable to the handle assembly and the end effector. The surgical device adapter also includes a drive coupling selectively couplable to the handle assembly. The drive coupling assembly includes a retraction assembly movable from a first configuration to a second configuration, wherein in the first configuration the retraction assembly is disengaged from the drive mechanism and in the second configuration the refraction assembly is engaged with the drive mechanism and prevents coupling of the handle assembly to the surgical device adapter.

According to one aspect of the above embodiment, the drive coupling assembly is configured to rotate about a longitudinal axis defined by the surgical device adapter and relative to the housing such that when the retraction assembly is in the second configuration, rotation of the drive coupling assembly actuates the drive mechanism.

According to one aspect of the above embodiment, the retraction assembly includes: a lock rocker pivotally coupled within the drive coupling assembly; and a lock ring rotatable about the longitudinal axis and relative to the drive coupling assembly, wherein upon rotation thereof the lock ring is configured to actuate the lock rocker to engage with the drive mechanism.

According to one aspect of the above embodiment, the lock rocker further includes a first proximally facing stop member configured to abut the surgical device to prevent coupling thereof to the handle assembly when the refraction assembly is in the second configuration.

According to one aspect of the above embodiment, the retraction assembly further includes a spring-loaded lock bolt slidably coupled to the drive coupling and engaged with the lock ring, the lock bolt configured to prevent rotation of the lock ring.

According to one aspect of the above embodiment, the lock bolt further includes a second proximally facing stop member configured to abut the surgical device to prevent coupling thereof to the handle assembly when the refraction assembly is in the second configuration.

According to one aspect of the above embodiment, the drive coupling assembly includes at least one latch pivotally coupled therein and configured to engage the handle assembly.

According to one embodiment of the present disclosure, a surgical device adapter for coupling an end effector to a handle assembly is provided. The surgical device adapter includes: a housing; a drive mechanism disposed within the housing and couplable to the handle assembly and the end effector; and a retraction assembly rotationally coupled to the drive mechanism. The retraction assembly is configured to: rotate about a longitudinal axis defined by the surgical device adapter in response to rotation of the drive mechanism; and rotate the drive mechanism in response to rotation thereof.

According to one aspect of the above embodiment, the drive mechanism includes a drive shaft coupled to the end effector and configured to actuate the first and second jaws, the drive shaft non-rotatably supporting a gear.

According to one aspect of the above embodiment, the retraction assembly includes a retraction gear including an inner geared surface meshingly engaged with the gear.

According to one aspect of the above embodiment, the retraction gear includes a latch pivotally coupled thereto about a pivot, wherein the latch is movable from a closed configuration in which the latch is formed about the retraction gear and an open configuration in which the latch radially extends from the retraction gear.

According to one aspect of the above embodiment, the latch includes a stop feature disposed adjacent the pivot to limit pivoting of the latch relative to the retraction gear.

According to one aspect of the above embodiment, the retraction gear includes a grip surface along at least a portion of an outer surface thereof.

According to one embodiment of the present disclosure, a surgical device is provided. The surgical device includes: an end effector including a first jaw and a second jaw moveable relative to the first jaw; a handle assembly including at least one motor mechanically coupled to the jaw assembly; and an adapter assembly removably coupled to a proximal end of the jaw assembly and a distal end of the handle assembly. The adapter assembly includes: a housing; a drive mechanism disposed within the housing and configured to couple the at least one motor to the end effector; and a drive coupling assembly selectively couplable to the handle assembly. The drive coupling assembly includes a retraction assembly movable from a first configuration to a second configuration, wherein in the first configuration the retraction assembly is disengaged from the drive mechanism and in the second configuration the retraction assembly is engaged with the drive mechanism and prevents coupling of the handle assembly to the surgical device adapter.

According to one aspect of the above embodiment, the drive coupling assembly is configured to rotate about a longitudinal axis defined by the surgical device adapter and relative to the housing such that when the retraction assembly is in the second configuration rotation of the drive coupling assembly actuates the drive mechanism.

According to one aspect of the above embodiment, the retraction assembly of the adapter assembly includes: a lock rocker pivotally coupled within the drive coupling assembly; and a lock ring rotatable about the longitudinal axis and relative to the drive coupling assembly, wherein upon rotation thereof the lock ring is configured to actuate the lock rocker to engage with the drive mechanism.

According to one aspect of the above embodiment, the lock rocker of the retraction assembly includes a first proximally facing stop member configured to abut the surgical device to prevent coupling of the adapter assembly to the handle assembly when the retraction assembly is in the second configuration.

According to one aspect of the above embodiment, the retraction assembly further includes a spring-loaded lock bolt slidably coupled to the drive coupling and engaged with the lock ring, the lock bolt configured to prevent rotation of the lock ring.

According to one aspect of the above embodiment, the lock bolt of the retraction assembly includes a second proximally facing stop member configured to abut the surgical device to prevent coupling of the adapter assembly to the handle assembly when the retraction assembly is in the second configuration.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
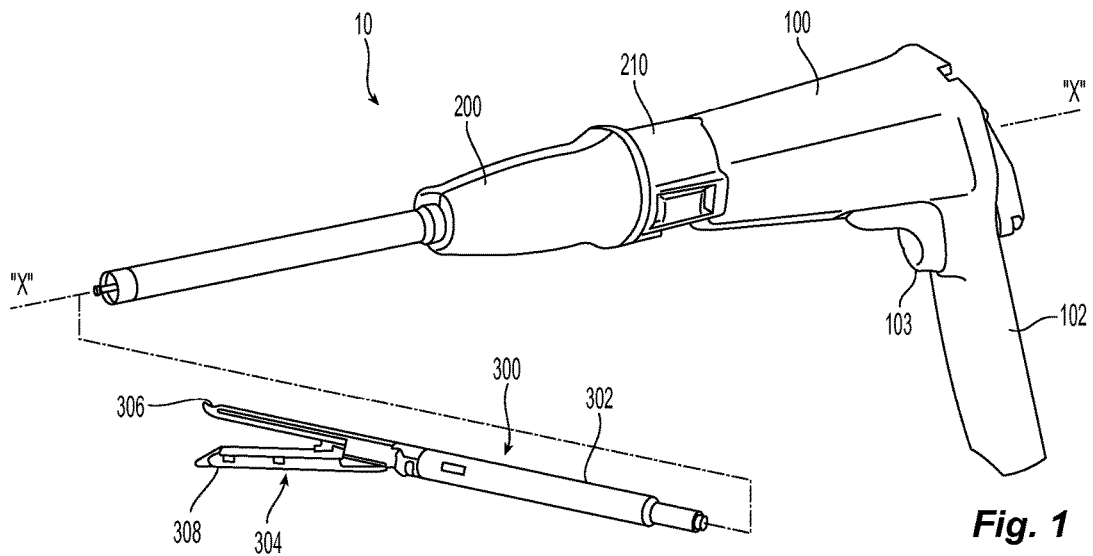
FIG. 1 is a perspective view of an electromechanical surgical system including a surgical instrument, an end effector and an adapter assembly according to the present disclosure.

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user. The terms "left" and "right" refer to that portion of the electromechanical surgical system, apparatus and/or device, or component thereof, that are on the left and right sides, respectively, from the perspective of the user facing the distal end of the electromechanical surgical system, apparatus and/or device from the proximal end while the surgical system, apparatus and/or device is oriented in non-rotational (e.g., home) configuration.

Figure 2:
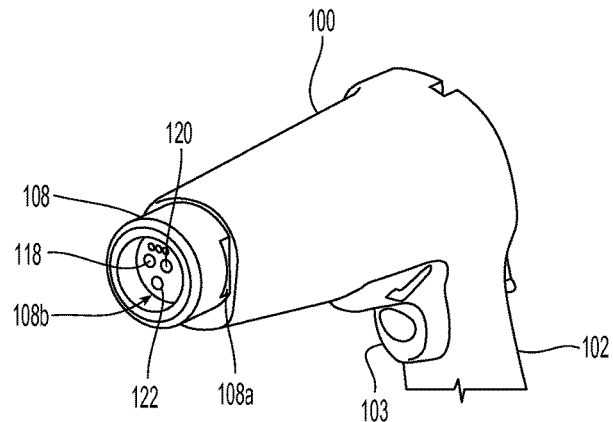
FIG. 2 is a perspective, front view of the surgical instrument of FIG. 1, according to the present disclosure.
Figure 3:
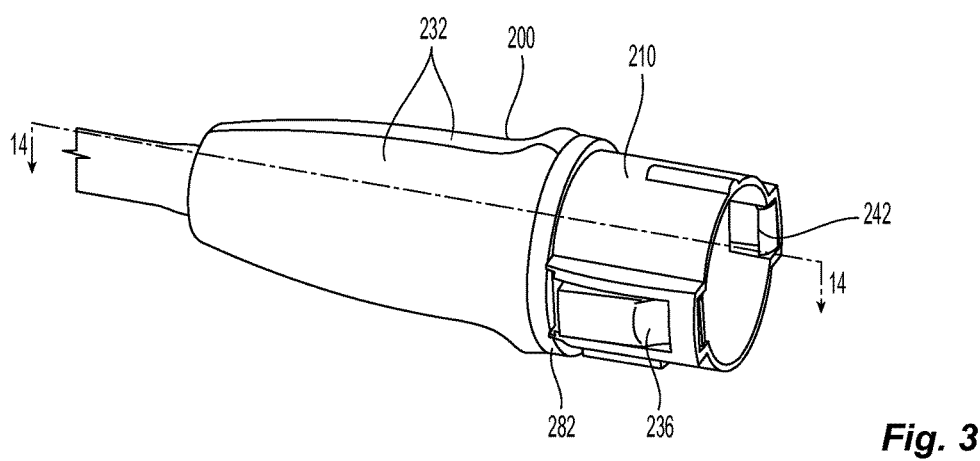
FIG. 3 is a perspective, rear view of the adapter assembly of FIG. 1, according to the present disclosure.

Referring initially to FIGS. 1-3, an electromechanical, hand-held, powered surgical system, in accordance with an embodiment of the present disclosure is shown and generally designated 10. Electromechanical surgical system 10 includes a surgical apparatus or device in the form of an electromechanical, hand-held, powered surgical instrument 100 that is configured for selective attachment thereto of a plurality of different end effectors 300, via an adapter assembly 200 (e.g., elongated body). The end effector 300 and the adapter assembly 200 are configured for actuation and manipulation by the electromechanical, hand-held, powered surgical instrument 100. In particular, the surgical instrument 100, the adapter assembly 200, and the end effector 300 are separable from each other such that the surgical instrument 100 is configured for selective connection with adapter assembly 200, and, in turn, adapter assembly 200 is configured for selective connection with any one of a plurality of different end effectors 300.

Reference may be made to International Application No. PCT/US2008/077249, filed Sep. 22, 2008 (Inter. Pub. No. WO 2009/039506) and U.S. Patent Application Publication No. 2011/0121049 published May 26, 2011, the entire contents of all of which are incorporated herein by reference, for a detailed description of the construction and operation of exemplary electromechanical, hand-held, powered surgical instrument 100.

As illustrated in FIGS. 1 and 2, surgical instrument 100 includes a handle housing 102 including one or more controllers, a power source, and a drive mechanism having one or more motors, gear selector boxes, gearing mechanisms, and the like. The housing 102 also supports a control assembly 103. Control assembly 103 may include one or more finger-actuated control buttons, rocker devices, joystick or other directional controls, whose input is transferred to the drive mechanism to actuation the adapter assembly 200 and the end effector 300.

In particular, drive mechanism is configured to drive shafts and/or gear components in order to selectively move tool assembly 304 of end effector 300 relative to proximal body portion 302 of end effector 300, to rotate end effector 300 about a longitudinal axis "X-X" (FIG. 1) defined by the adapter assembly 200 relative to handle housing 102, to move anvil assembly 306 relative to cartridge assembly 308 of end effector 300, and/or to fire a stapling and cutting cartridge within cartridge assembly 308 of end effector 300.

With continued reference to FIG. 2, the housing 102 defines a nose or connecting portion 108 configured to accept a corresponding drive coupling assembly 210 of adapter assembly 200. The connecting portion 108 of surgical instrument 100 has a cylindrical recess 108b that receives the drive coupling assembly 210 of adapter assembly 200 when adapter assembly 200 is mated to surgical instrument 100. Connecting portion 108 houses one or more rotatable drive connectors that interface with corresponding rotatable connector sleeves of the adapter assembly 200 as described in further detail below. The surgical instrument 100 includes rotatable drive connector 118, 120, 122 disposed within the connecting portion 108 that are actuated by the drive mechanism.

Figure 4:
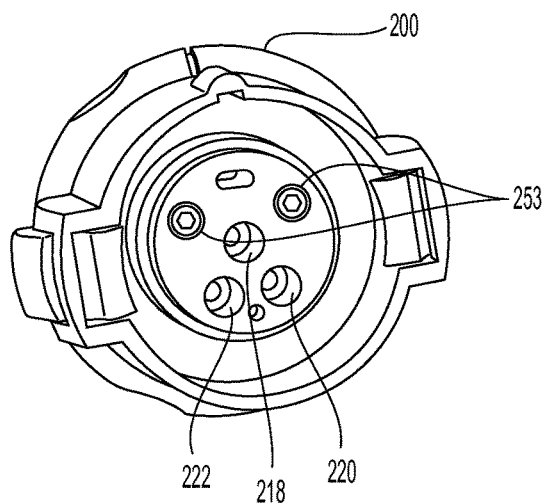
FIG. 4 is a perspective, rear view of the adapter assembly of FIG. 1, according to the present disclosure.

With reference to FIGS. 2 and 4, when adapter assembly 200 is mated to surgical instrument 100, each of rotatable drive connectors 118, 120, 122 of surgical instrument 100 couples with a corresponding rotatable connector sleeve 218, 220, 222 of adapter assembly 200. In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical instrument 100 causes a corresponding rotation of the corresponding connector sleeve 218, 220, 222 of adapter assembly 200.

The mating of drive connectors 118, 120, 122 of surgical instrument 100 with connector sleeves 218, 220, 222 of adapter assembly 200 allows rotational forces to be independently transmitted via each of the three respective connector interfaces. The drive connectors 118, 120, 122 of surgical instrument 100 are configured to be independently rotated by drive mechanism.

Since each of drive connectors 118, 120, 122 of surgical instrument 100 has a keyed and/or substantially non-rotatable interface with respective connector sleeves 218, 220, 222 of adapter assembly 200, when adapter assembly 200 is coupled to surgical instrument 100, rotational force(s) are selectively transferred from drive mechanism of surgical instrument 100 to adapter assembly 200.

The selective rotation of drive connector(s) 118, 120 and/or 122 of surgical instrument 100 allows surgical instrument 100 to selectively actuate different functions of end effector 300. As discussed in greater detail below, selective and independent rotation of first drive connector 118 of surgical instrument 100 corresponds to the selective and independent opening and closing of tool assembly 304 of end effector 300, and driving of a stapling/cutting component of tool assembly 304 of end effector 300. Also, the selective and independent rotation of second drive connector 120 of surgical instrument 100 corresponds to the selective and independent articulation of tool assembly 304 of end effector 300 about an articulation axis that is transverse to longitudinal axis "X-X" (FIG. 1). In particular, the end effector 300 defines a second or respective longitudinal axis and is movable from a first position in which the second or respective longitudinal axis is substantially aligned with the first longitudinal axis "X-X" defined by the adapter assembly 200 to at least a second position in which the second or respective longitudinal axis is disposed at a non-zero angle with respect to the first longitudinal axis "X-X." Additionally, the selective and independent rotation of third drive connector 122 of surgical instrument 100 corresponds to the selective and independent rotation of end effector 300 about longitudinal axis "X-X" (FIG. 1) relative to handle housing 102 of surgical instrument 100.

Figure 5:
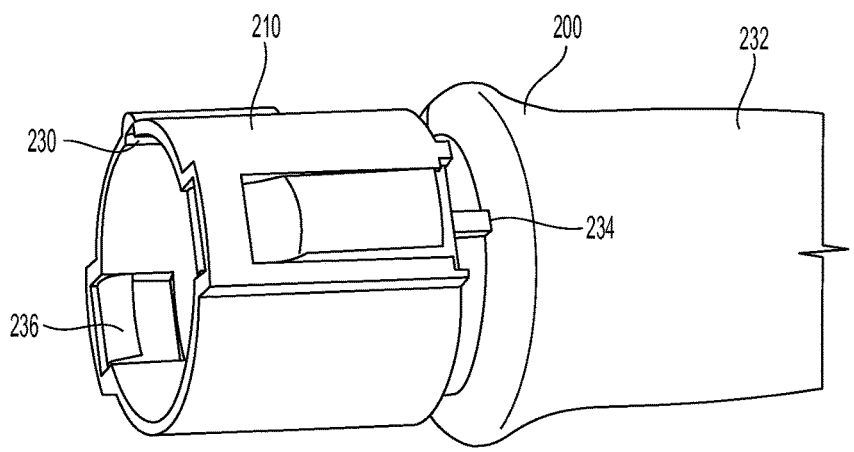
FIG. 5 is a further perspective, rear view of the adapter assembly of FIG. 1, according to the present disclosure.
Figure 20:
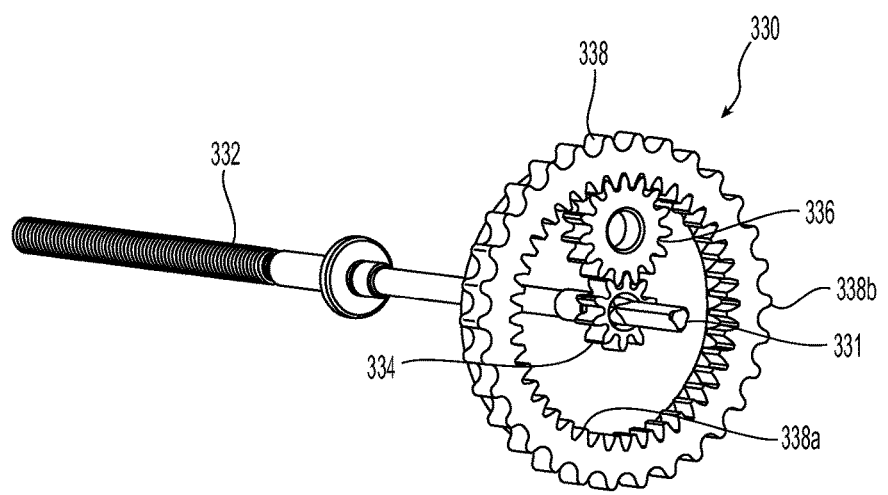
FIG. 20 is a perspective, partially-disassembled view of the drive mechanism of FIG. 17, according to the present disclosure.
Figure 21:
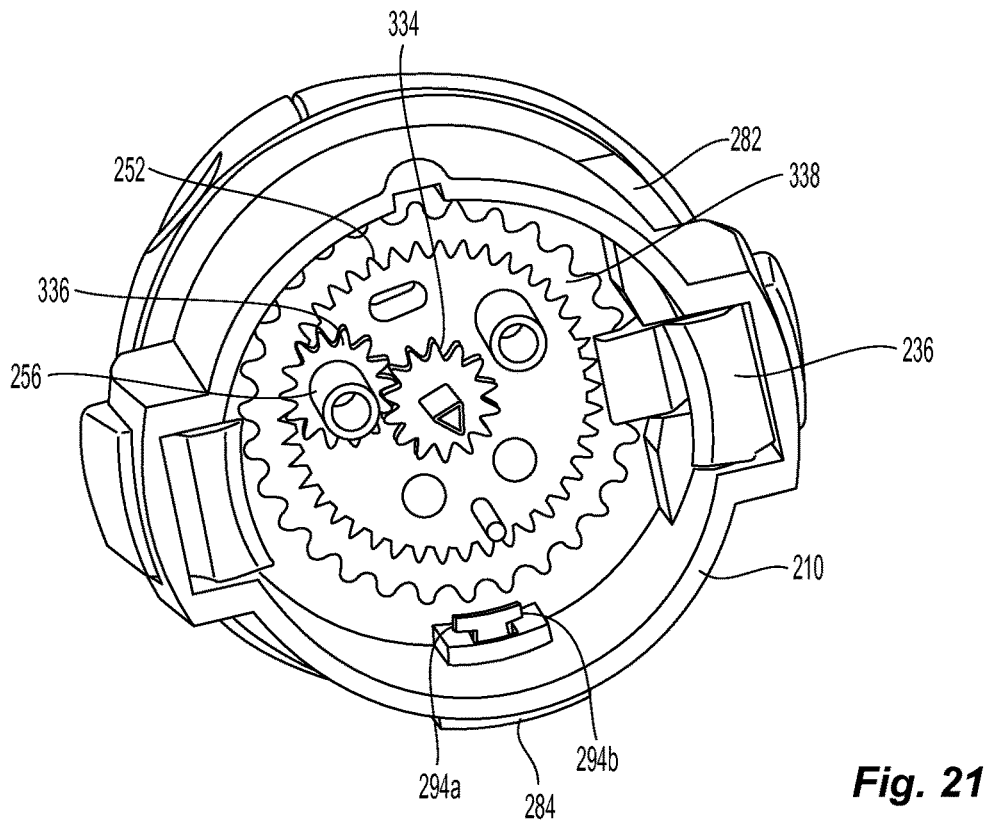
FIG. 21 is a rear, partially-disassembled view of the adapter assembly of FIG. 15, according to the present disclosure.

With reference to FIGS. 3 and 5, the drive coupling assembly 210 of adapter assembly 200 includes an orienting groove 230 for orienting the adapter assembly 200 to the instrument 100. The adapter assembly 200 also includes an adapter housing 232 coupled to the coupling assembly 210 and enclosing a drive mechanism 330 as described in further detail below with respect to FIGS. 20 and 21. In embodiments, the drive coupling assembly 210 may be removably coupled to the drive housing 232 and also includes an orienting assembly 234 for orienting the adapter assembly 200 to the drive housing 232. This allows the drive coupling assembly 210 to rotate independently of adapter housing 232 during manual rotation as described in further detail below. The adapter housing 232 may include two half portions interconnected via fasteners 233 (FIG. 14).

Figure 6:
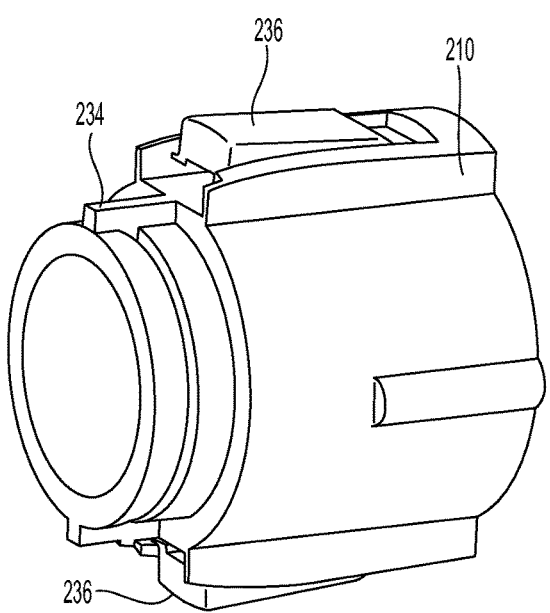
FIG. 6 is a perspective view of a drive coupling of the adapter assembly of FIG. 1, according to the present disclosure.
Figure 7:
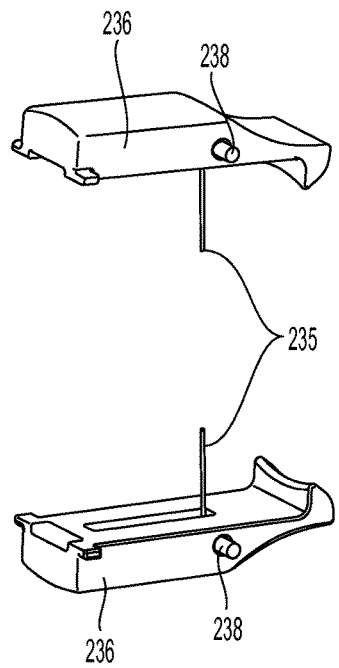
FIG. 7 is a perspective view of a pair of opposing latches of the drive coupling of FIG. 6, according to the present disclosure.
Figure 8:
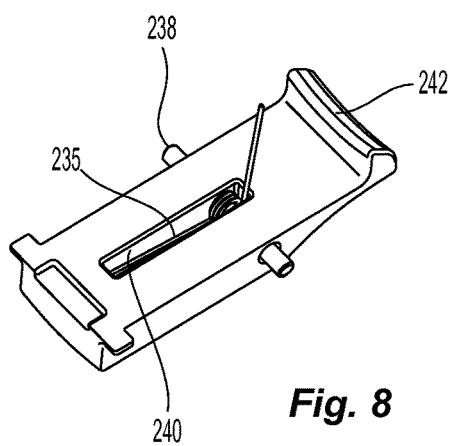
FIG. 8 is a perspective view of one latch of the pair of latches of FIG. 7, according to the present disclosure.

With reference to FIGS. 6-8, the drive coupling assembly 210 includes a pair of opposing, spring-loaded latches 236. Each of the latches 236 includes a tooth 242, a pivot pin 238 pivotally coupling the latch 236 to the drive coupling assembly 210, and defines a slot 240 for enclosing a spring 235. The latches 236 automatically rotate/pivot open when they engage corresponding slots 108a of the connecting portion 108 (FIG. 2) with the teeth 242. To disengage the drive coupling assembly 210 from the connecting portion 108 of the housing 102, the latches 236 are pressed down, thereby pivoting the latches 236 and lifting the teeth 242 from the slots 108a of the connecting portion 108.

Figure 9:
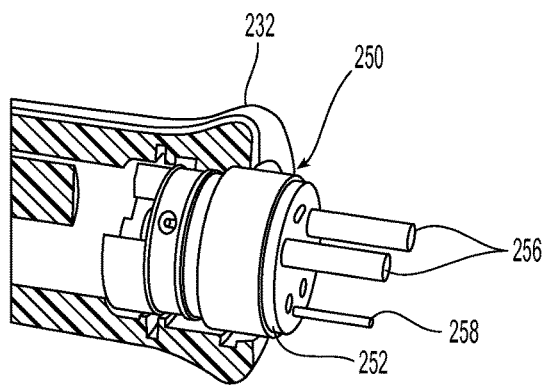
FIG. 9 is a perspective, partially-disassembled view of the adapter assembly of FIG. 1, according to the present disclosure.
Figure 10:
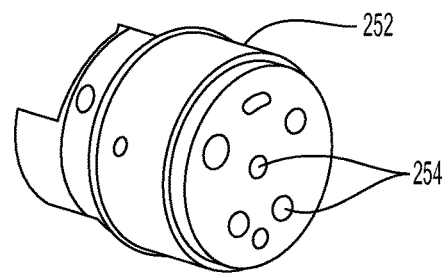
FIG. 10 is a perspective view of a proximal housing block of the adapter assembly of FIG. 1, according to the present disclosure.
Figure 11:
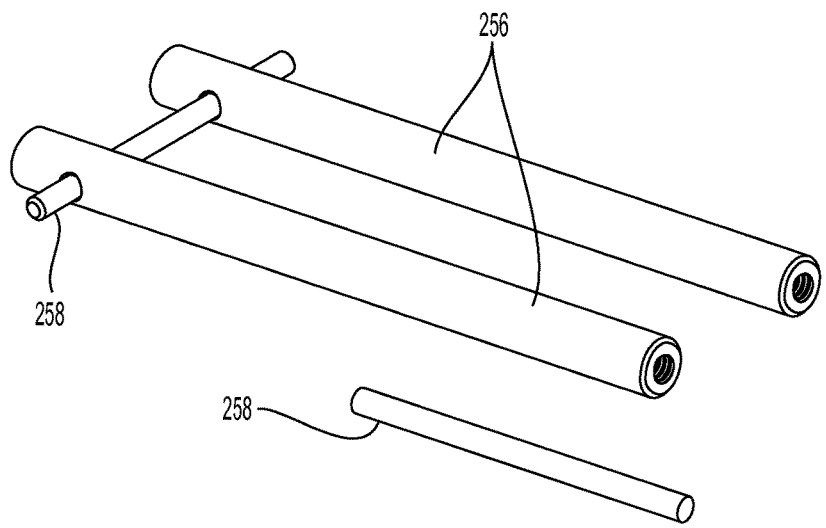
FIG. 11 is a perspective view of shafts and a pin of the adapter assembly of FIG. 1, according to the present disclosure.

FIGS. 9-11 illustrate a drive assembly 250 of the adapter assembly 200. The drive assembly 250 includes a distal housing block 252 having a substantially cylindrical body enclosed within the housing 232. The block 252 includes a plurality of openings 254 therein, which may be threaded, or may include threaded shafts 256 to guide drive shafts (not shown) therethrough. The drive shafts may be coupled to the corresponding rotatable connector sleeve 218, 220, 222 of adapter assembly 200. The block 252 may also include additional pins 258 to provide structural integrity. The shafts 256 also act as thermal conductors during autoclaving to sterilize the drive shafts.

Figure 12:
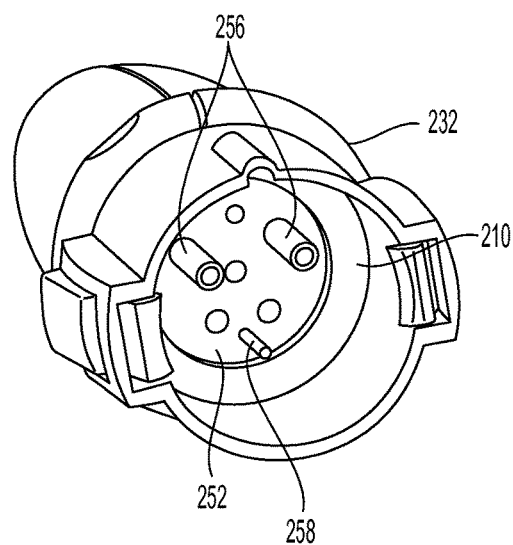
FIG. 12 is a rear, partially-disassembled view of the adapter assembly of FIG. 1, according to the present disclosure.
Figure 13:
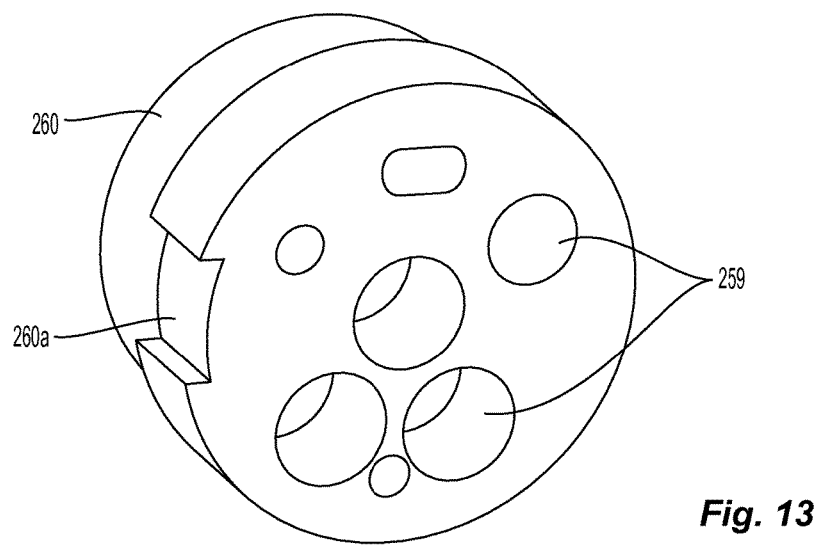
FIG. 13 is a perspective view of a proximal housing block of the adapter assembly of FIG. 1, according to the present disclosure.
Figure 14:
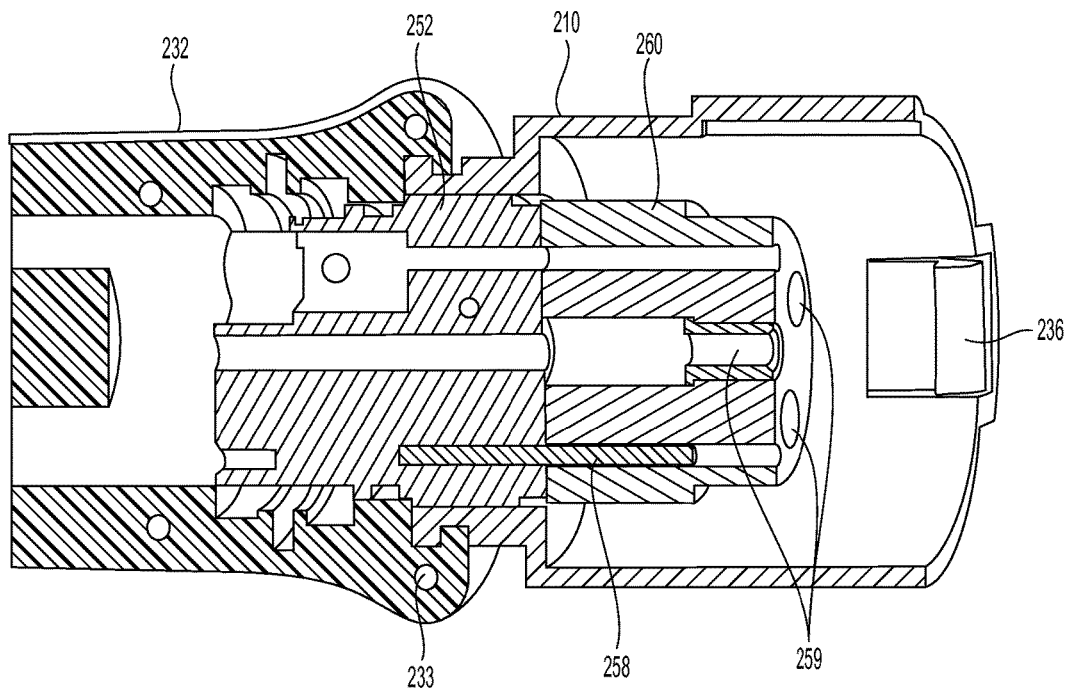
FIG. 14 is a cross-sectional, side view of the adapter assembly of FIG. 1, taken across the lines 14-14 of FIG. 3, according to the present disclosure.
Figure 15:
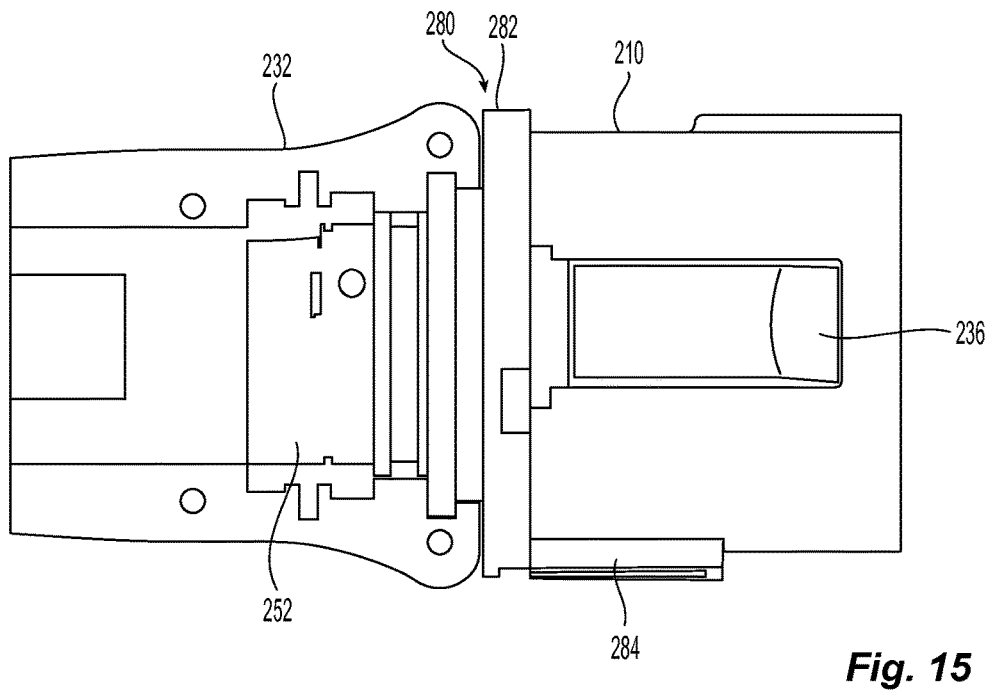
FIG. 15 is a partially-disassembled, side view of the drive coupling assembly including a retraction assembly and the adapter assembly of FIG. 1, according to the present disclosure.
Figure 16:
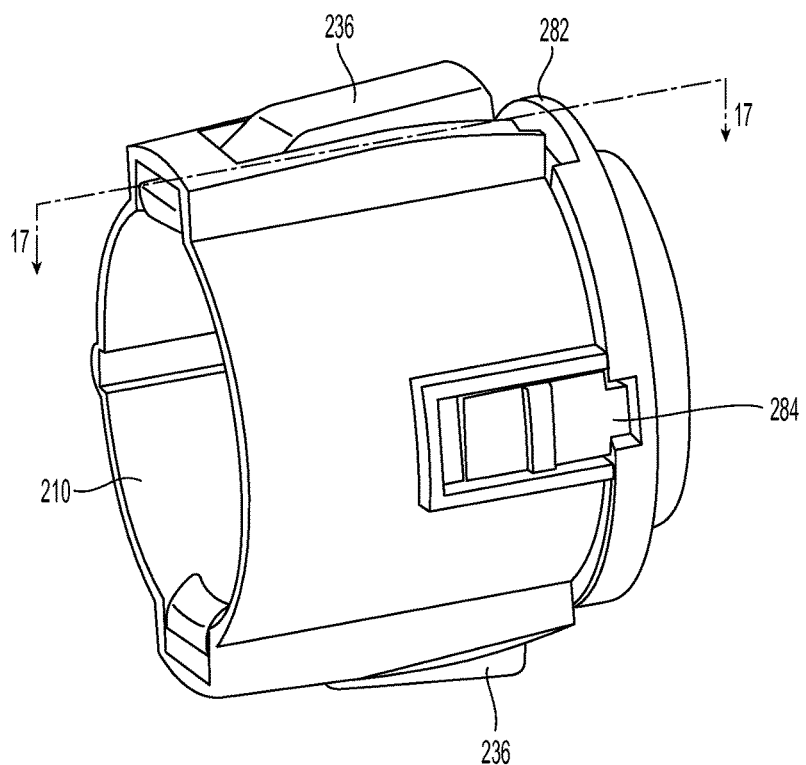
FIG. 16 is a perspective view of the drive coupling assembly of FIG. 15, according to the present disclosure.

FIGS. 4 and 12-14 illustrate final assembly of the adapter assembly 200. FIG. 12 shows the drive coupling assembly 210 coupled to the adapter housing 232. A distal housing block 260 (FIG. 13) is thereafter coupled to the distal housing block 252 as shown in FIG. 4. As shown in FIGS. 13 and 14, the proximal housing 260 also includes a plurality of openings 259 therethrough configured to mate with the shafts 256 and the pin 258, which provide structural support for the housing blocks 252 and 260. Various fasteners 253 (e.g., screws, bolts, etc.) may be used to secure the housing blocks 252 and 260 (FIG. 4).

With reference to FIGS. 3 and 15-19, the adapter assembly 200 also includes a first retraction assembly 280 disposed within the drive coupling assembly 210 for manually reversing the drive mechanism 330. In particular, the retraction assembly 280 is configured to reverse the clamp and firing strokes of the adapter assembly 200 by retracting or reversing rotation of an actuation drive shaft 332 (FIG. 20) coupled to the corresponding rotatable connector sleeve 218 of adapter assembly 200.

The retraction assembly 280 includes a lock ring 282, a spring-loaded lock bolt 284, and a lock rocker 285. The lock ring 282 is used to manually engage the lock rocker 285 with the drive mechanism 330 such that continual clockwise rotation of the lock ring 282 reverses the drive mechanism 330 as described in further detail below. The lock bolt 284 is a safety mechanism, which prevents accidental engagement of the lock ring 282 with the drive mechanism 330. The lock bolt 284 is spring-loaded and is thereby continually engaged with the lock ring 282 until it is pulled proximally to allow for actuation of the lock ring 282.

With reference to FIGS. 17-21, the drive mechanism 330 (FIG. 20) of the adapter assembly 200 is shown. The drive mechanism 330 includes the drive shaft 332 having a keyed distal end 331 dimensioned and configured to engage the connector sleeve 218 such that rotation thereof is transferred to the drive shaft 332. The drive shaft 332 also includes a spur gear 334 that is meshingly engaged with an idler gear 336. The drive mechanism 330 further includes an outer gear 338 having an inner gearing surface 338a and an outer gearing surface 338b. The idler gear 336 is rotationally disposed over one of the shafts 256 and acts as a planetary gear interconnecting the spur gear 334 with the outer gear 338 thereby allowing for transfer of rotational motion from the spur gear 334 to the outer gear 338. The outer gear 338 is freely rotatable unless engaged by the lock ring 282, as described in further detail below.

Figure 17:
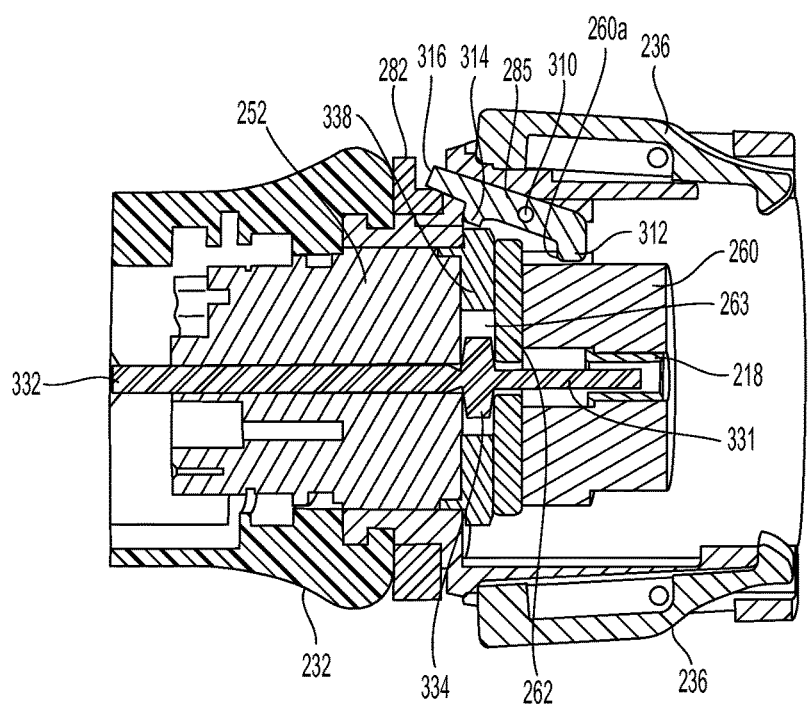
FIG. 17 is a cross-sectional view of the adapter assembly of FIG. 15, taken along the line 17-17 of FIG. 16, with a lock rocker of the retraction assembly disengaged from a drive mechanism, according to the present disclosure.
Figure 18:
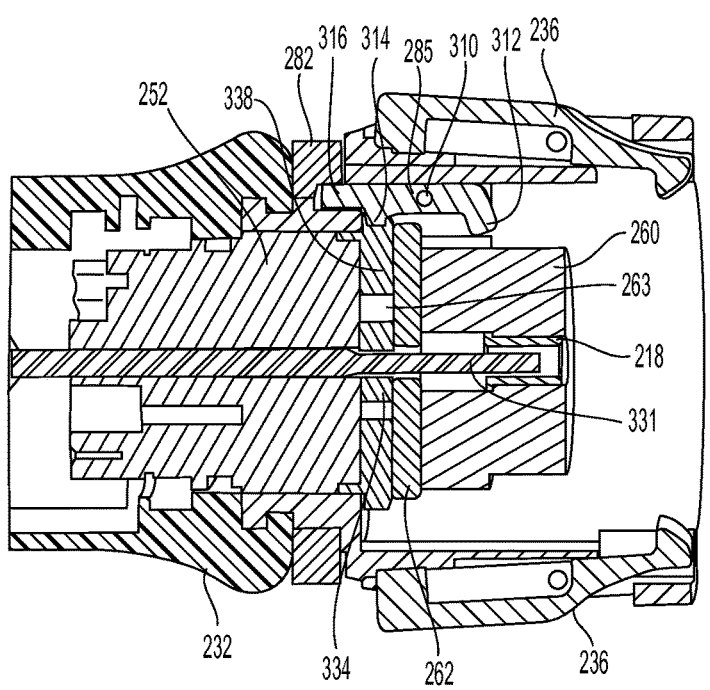
FIG. 18 is a cross-sectional view of the adapter assembly of FIG. 15, taken along the line 17-17 of FIG. 16, with the lock rocker of the retraction assembly engaged to the drive mechanism, according to the present disclosure.
Figure 19:
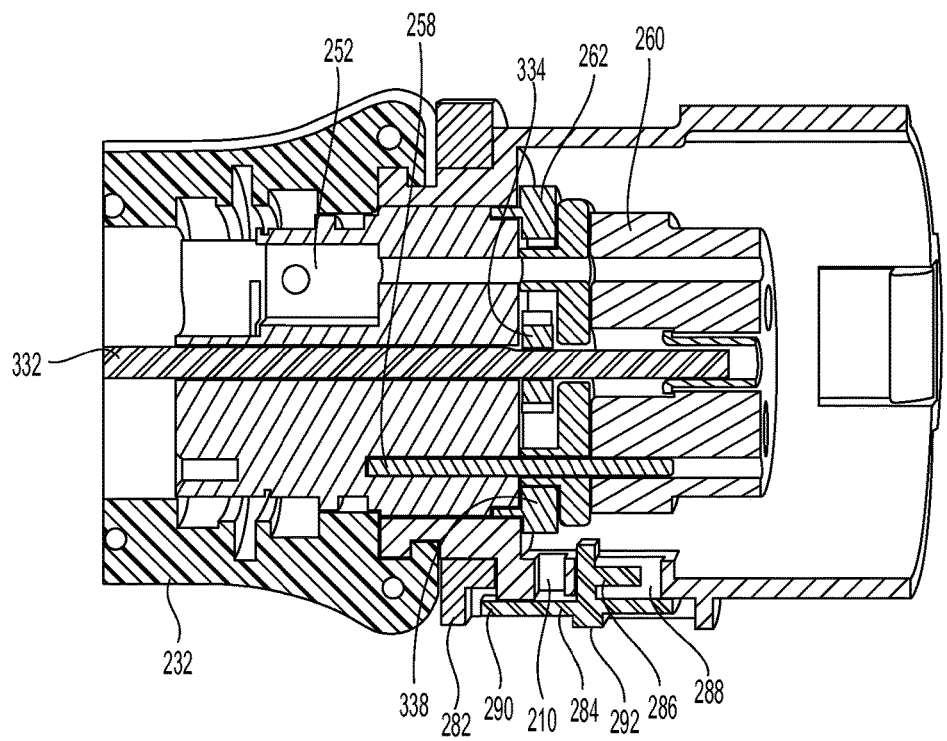
FIG. 19 is a cross-sectional view of the adapter assembly of FIG. 15, taken along the line 14-14 of FIG. 3, with a lock bolt engaged with a lock ring of the retraction assembly, according to the present disclosure.
Figure 22:
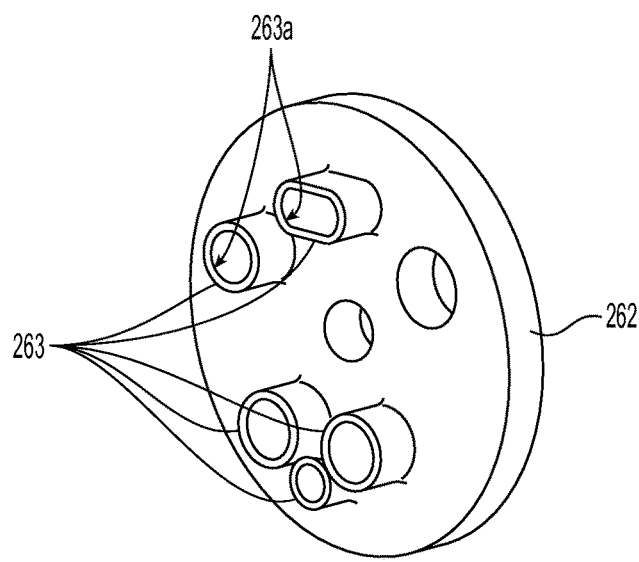
FIG. 22 is a perspective view of a spacer, according to the present disclosure.
Figure 23:
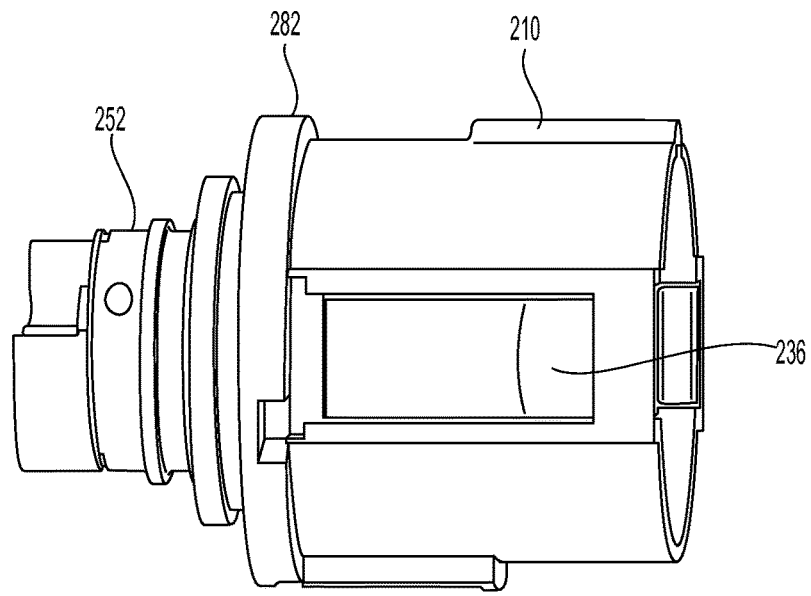
FIG. 23 is a side, partially-disassembled view of the adapter assembly of FIG. 15, according to the present disclosure.

With reference to FIGS. 15 and 21-24, assembly of the drive mechanism 330 and the retraction assembly 280 are illustrated. As shown in FIGS. 17-19, the gears 334, 336, 338 are disposed between the distal and proximal housing blocks 252 and 260. As shown in FIG. 23, initially, the lock ring 282 is inserted over the distal end of the drive coupling assembly 210, which is then inserted into the proximal housing block 252. The housing 232 (e.g., two mated halves) is then coupled to the proximal housing block 252. The drive mechanism 330 is then inserted into the proximal housing block 252 (FIG. 21) followed by a spacer 262 (FIG. 22).

Figure 25:
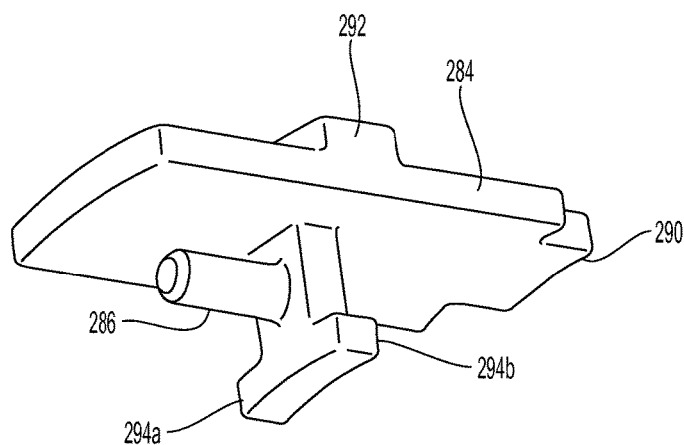
FIG. 25 is a perspective view of the lock bolt of FIG. 19, according to the present disclosure.

With reference to FIG. 22, the spacer 262 is disposed between the proximal and distal housing blocks 252 and 260 providing for adequate clearance for the gears 334, 336, 338 to rotate as described above. The spacer 262 includes a plurality of cylindrical surface features 263 having openings 263a therein for the passage of the shafts 256 and the pin 258 therethrough. As shown in FIG. 25, during assembly, the drive mechanism 330 including the gears 334, 336, 338 are disposed over the proximal end of the distal housing block 252 and the spacer 262 is inserted over the gears 334, 336, 338, followed by the distal housing block 260, which are then secured as described above.

With reference to FIGS. 19 and 25, the lock bolt 284 includes a proximally-facing post 286 having a spring 288 disposed thereon, which biases the lock bolt 284 in a distal direction. The lock bolt 284 also includes a feature 290 for interfacing with the lock ring 282, as described in further detail below, and a grip feature 292 allowing for better grip by the user. The lock bolt 284 further includes opposing, laterally-facing tabs 294a, 294b for slidable coupling of the lock bolt 284 to the drive coupling assembly 210.

Figure 24:
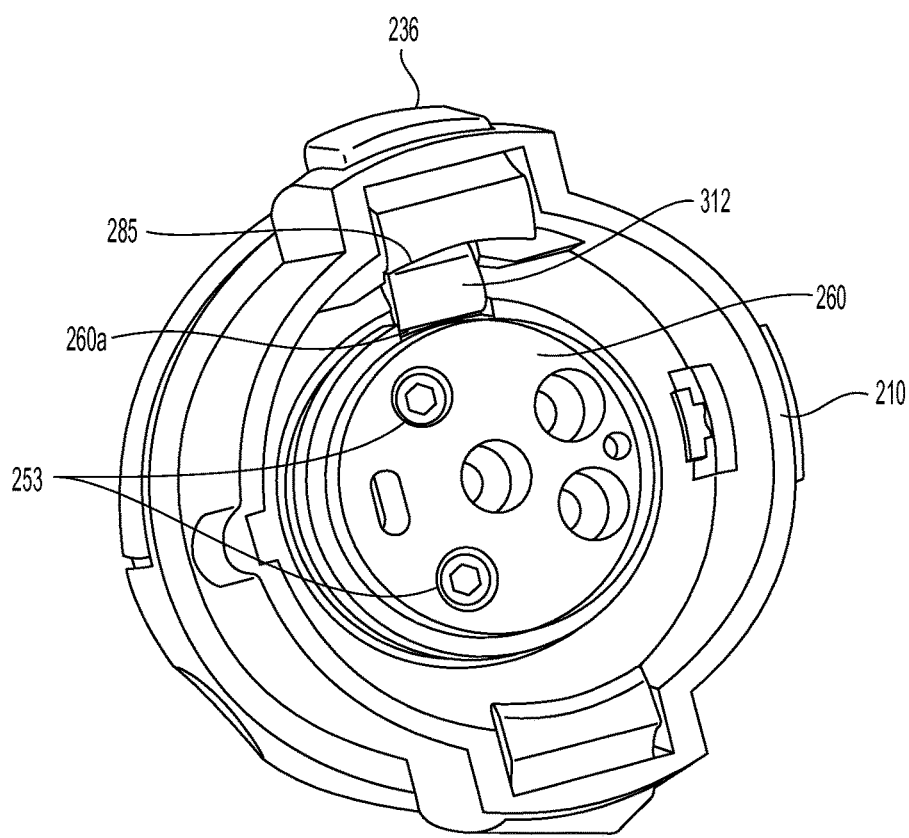
FIG. 24 is a rear view of the adapter assembly of FIG. 15, according to the present disclosure.
Figure 26:
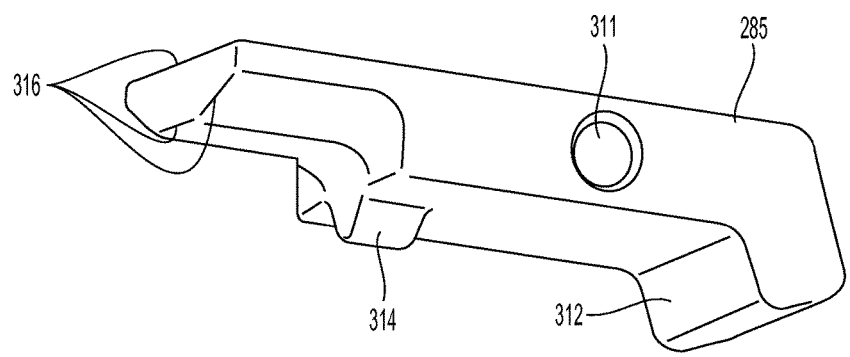
FIG. 26 is a perspective view of the lock rocker of FIG. 17, according to the present disclosure.
Figure 27:
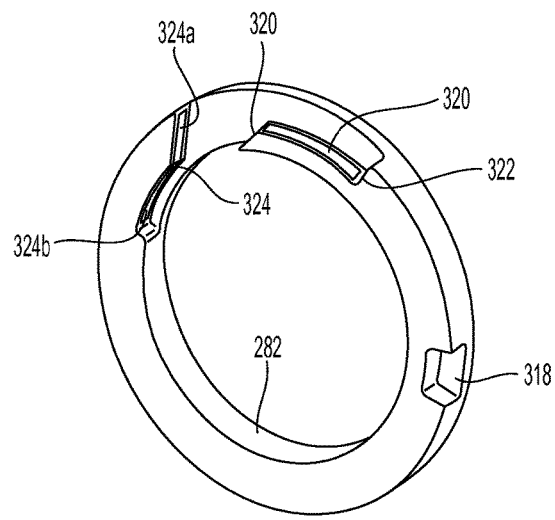
FIG. 27 is a perspective view of the lock ring of FIG. 19, according to the present disclosure.

With reference to FIGS. 17, 18, and 26, the lock rocker 285 includes a pivot pin 310 disposed within an opening 311 pivotally coupling the lock rocker 285 to the drive coupling assembly 210 beneath one of the latches 236. The lock rocker 285 includes a latching feature 312 disposed at a proximal end thereof, a tooth feature 314 disposed distally of the pivot pin 310, and a camming feature 316 disposed at a distal end thereof. As shown in FIGS. 17 and 24, the latching feature 312 is configured to engage a slot 260a disposed on the distal housing block 260. As shown in FIG. 18, the tooth feature 314 of the lock rocker 285 is configured to engage the outer gearing surface 338b of the outer gear 338 and the camming feature 316 of the lock rocker 285 is configured to engage the lock ring 282.

With reference to FIGS. 16-19 and 27, the lock ring 282 includes a radial slot 318 configured and dimensioned for engaging the feature 290 of the lock bolt 284. The lock ring 282 also includes first and second camming surfaces 320, 324 formed therein for engaging the camming feature 316 of the lock rocker 285. As shown in FIGS. 17 and 24, the first camming surface 320 is disposed on an inner circumference of the lock ring 282 and maintains the lock rocker 285 engaged with the distal housing block 260. The first camming surface 320 also includes an abutment surface 322 configured and dimensioned for engaging the feature 290 of the lock bolt 284 after the lock ring 282 has been rotated.

The second camming slot 324 is disposed on or formed in an outer circumference of the lock ring 282 and includes first and second camming portions 324a, 324b. As shown in FIG. 18, the second camming surface slot 324 is used to guide the lock rocker 285 into engagement with the outer gear 338 and described in further detail below.

Figure 28:
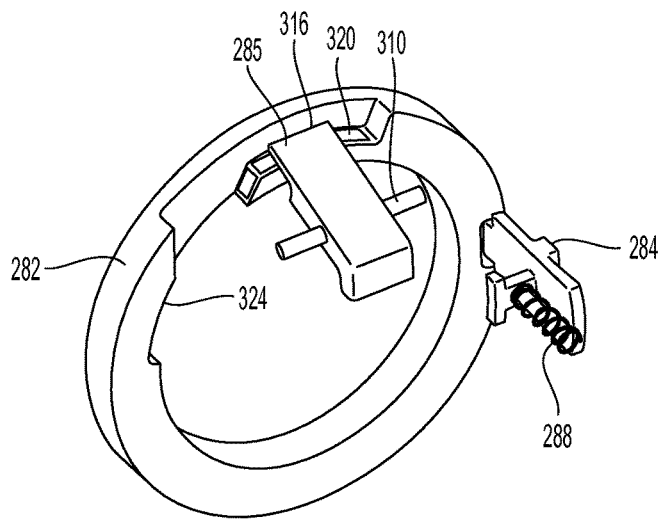
FIG. 28 is a perspective, partially-disassembled view of the retraction assembly of FIG. 17 in its home configuration, according to the present disclosure.

FIGS. 28-31 show operation of the retraction assembly 280. Retraction may be attempted following disconnection of the instrument 100 from the adapter assembly 200, e.g., in the event the instrument 100 should fail or become inoperable during a surgical procedure. FIGS. 17, 19, and 28 show the retraction assembly 280 in its so-called "home" configuration, in which the lock rocker 285 is disengaged from the drive mechanism 330. As shown in FIGS. 19 and 28, in the "home" configuration, the lock bolt 284 is biased by the spring 288 to engage the lock ring 282 at the slot 318, thereby preventing rotation of the lock ring 282. As shown in FIGS. 17, 25, and 28, the lock rocker 285, in turn, is engaged with the slot 260a of the distal housing block 260. The lock rocker 285, and in particular the camming feature 316 of the lock rocker 285 is initially engaged with the first camming surface 320 of the lock ring 282.

Figure 29:
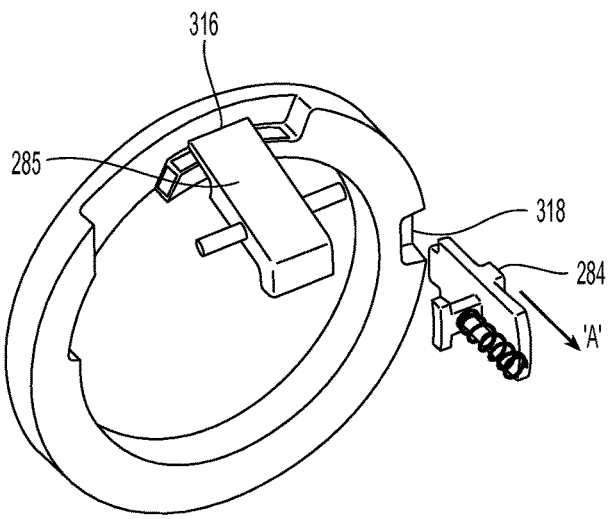
FIG. 29 is a perspective, partially-disassembled view of the retraction assembly of FIG. 17 with the lock bolt disengaged from the lock ring, according to the present disclosure.
Figure 30:
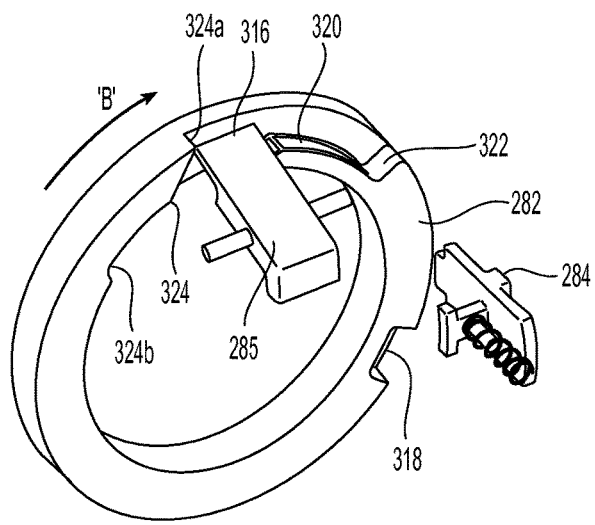
FIG. 30 is a perspective, partially-disassembled view of the retraction assembly of FIG. 17 with the lock ring partially-rotated, according to the present disclosure.

FIG. 29 shows the lock bolt 284 being disengaged from the lock ring 282 by pulling the lock bolt 284 proximally, as indicated by arrow "A," thus allowing for rotation of the lock ring 282 in a clockwise direction to begin the retraction process. With reference to FIG. 30, as the lock ring 282 is initially rotated, as indicated by arrow "B," the camming feature 316 of the lock rocker 285 is still engaged with the first camming surface 320 but travels along the first camming surface 320 and eventually contacts the first camming portion 324a of the second camming surface 320. As the rotation of the lock ring 282 is continued, the camming feature 316 of the lock rocker 285 continues to travel along the second camming portion 324b of the second camming surface 320. Concomitantly therewith, the lock bolt 284 is also reengaged with the lock ring 282 by the spring 288 and rests against the abutment surface 322.

Figure 31:
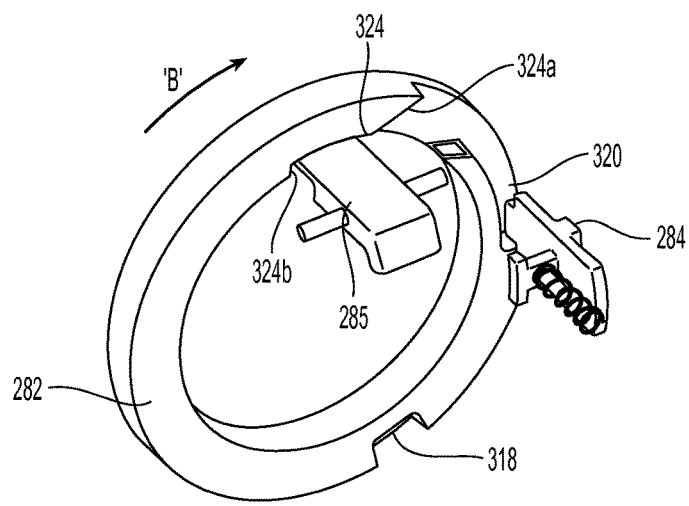
FIG. 31 is a perspective, partially-disassembled view of the retraction assembly of FIG. 17 with the lock ring fully rotated pivoting the lock rocker, according to the present disclosure.

FIGS. 18 and 31 show completed rotation of the lock ring 282 in which the drive coupling assembly 210 is engaged with the drive mechanism 330, namely, via the lock ring 282 to the outer gear 338. In operation, as the drive coupling assembly 210 is rotated relative to the drive housing 232, in a clockwise direction as indicated by arrow "B," along with the lock ring 282, the outer gear 338 is also rotated via the lock rocker 285. This in turn rotates the drive shaft 332 via the idler gear 334 and reverses and/or retracts the anvil assembly 306 relative to cartridge assembly 308 of end effector 300 that is connected to the distal end of adapter assembly 200. Once engaged, the drive coupling assembly 210 also prevents counterclockwise rotation of the lock ring 282 and any forward (e.g., clamping and/or firing) movement of the drive shaft 332. In embodiments, the drive coupling assembly 210 may be rotated manually or by a powered mechanism.

Figure 32:
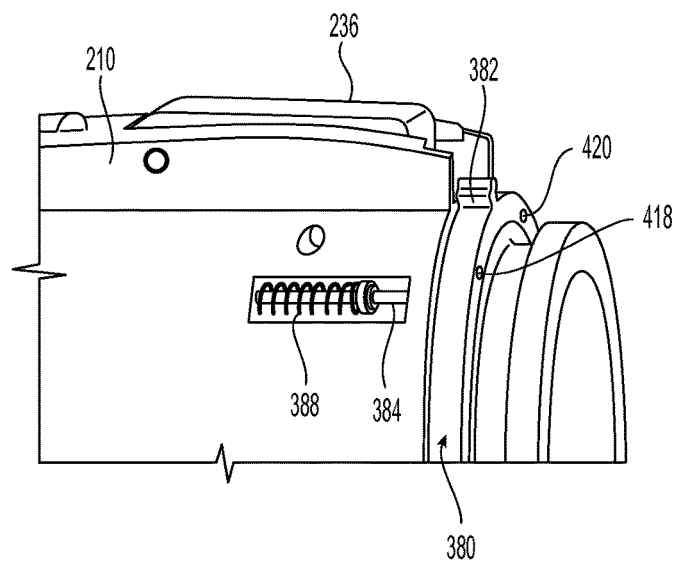
FIG. 32 is a side view of the drive coupling assembly with a retraction assembly according to another embodiment of the present disclosure.
Figure 33:
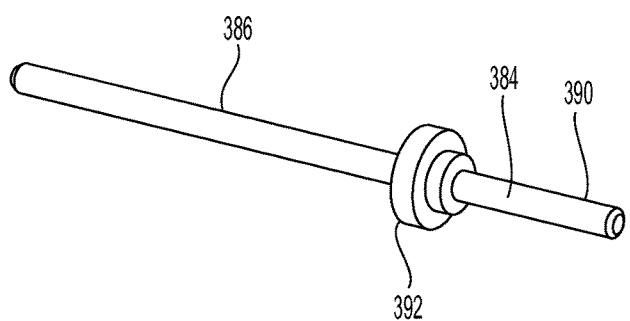
FIG. 33 is a perspective view of a lock bolt of the retraction assembly of FIG. 32, according to the present disclosure.
Figure 34:
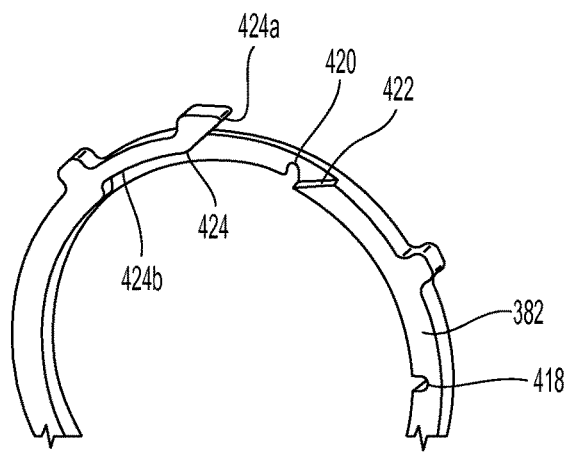
FIG. 34 is a perspective view of a lock ring of the retraction assembly of FIG. 32, according to the present disclosure.

FIGS. 32-34 show another embodiment of a retraction assembly 380, which is substantially similar to the retraction assembly 280 and only the differences therebetween are described. The retraction assembly 380 includes a lock ring 382, a spring-loaded lock bolt 384, and the lock rocker 285, which is unchanged.

With reference to FIGS. 32 and 33, the lock bolt 384 includes a proximally-facing post 386 having a spring 388 disposed therein, which biases the lock bolt 384 in a distal direction. The lock bolt 384 also includes a feature (e.g., post) 390 for interfacing with the lock ring 382 as described in further detail below and a grip feature 392 allowing for better grip by the user and also abutting the spring 388.

With reference to FIGS. 32 and 34, the lock ring 382 includes a first slot 418 configured and dimensioned for engaging the feature 390 of the lock bolt 384. The lock ring 382 also includes first and second camming surfaces 420, 424 for engaging the camming feature 316 of the lock rocker 285. As shown in FIG. 17, the first camming surface 320 is disposed on or formed in an inner circumference of the lock ring 382 and maintains the lock rocker 285 engaged with the distal housing block 260 with respect to the lock ring 282. The lock ring 382 also includes a second slot 420 configured and dimensioned for engaging the feature 390 of the lock bolt 384 after the lock ring 382 has been rotated. The second camming slot 424 is disposed on an outer circumference of the lock ring 382 and includes first and second camming portions 424a, 424b. The second camming surface slot 424 is used to guide the lock rocker 285 into engagement with the outer gear 338 as shown in FIG. 18 with respect to the lock ring 282.

The lock ring 382 is operated in a similar manner as the lock ring 282 as described above with respect to FIGS. 28-31. Initially, the lock bolt 384 is pulled proximally out of the first slot 418 and the lock ring 382 is rotated in a clockwise direction. After rotation of the lock ring 382 is completed, the lock rocker 285 is engaged with the drive mechanism 330, namely, the outer gear 338 thereof, as described above. The lock bolt 384 is also reengaged with the lock ring 382 by the spring 388, and the feature 390 of the lock bolt 384 engages the second slot 420 of the lock ring 382. The drive coupling assembly 210 is then rotated relative to the drive housing 232, in a clockwise direction as indicated by arrow "C," to retract/reverse the drive mechanism 330.

Figure 35:
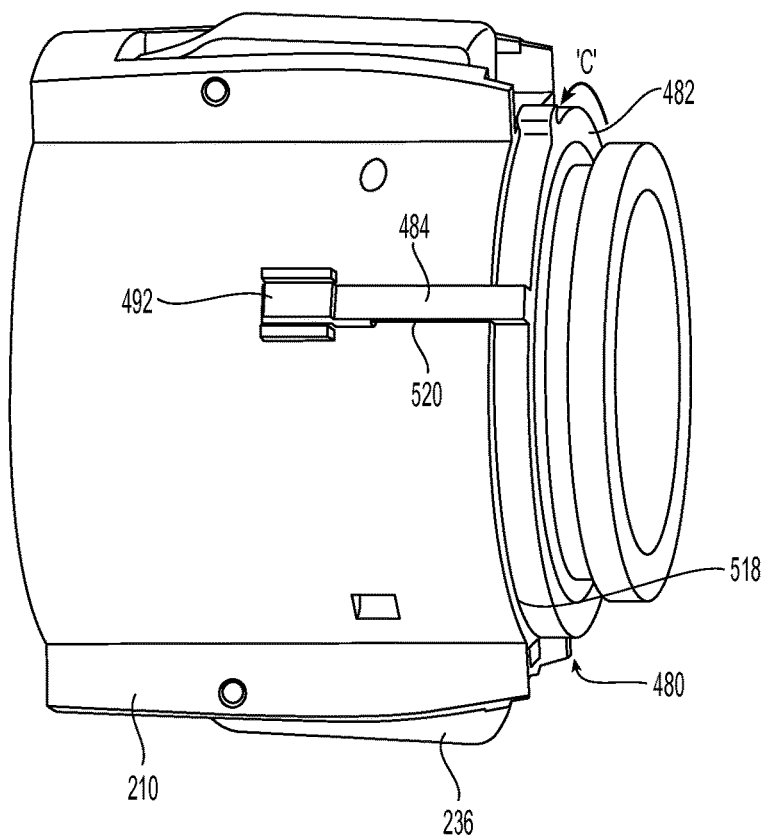
FIG. 35 is a side view of the drive coupling assembly with a retraction assembly according to another embodiment of the present disclosure.
Figure 36:
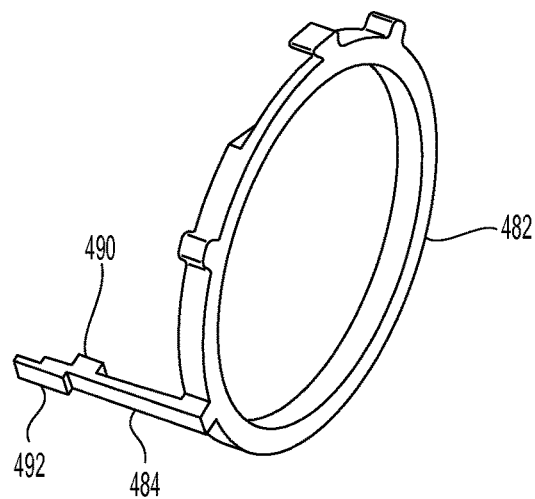
FIG. 36 is a perspective view of a lock ring of the retraction assembly of FIG. 35, according to the present disclosure.

FIGS. 35 and 36 show another embodiment of a retraction assembly 480, which is substantially similar to the retraction assembly 280 and only the differences therebetween are described. The retraction assembly 480 includes a lock ring 482 and the lock rocker 285, which is unchanged with respect to the retraction assembly 280. The lock ring 482 includes a flexible, resilient tab 484 coupled thereto, which performs the function of the lock bolts 284 and 384. The resilient tab 484 includes a feature (e.g., block) 490 for interfacing with first and second openings 518 and 520 defined on the outer surface of the device coupling assembly 210. The resilient tab 484 also includes a grip feature 492 allowing for better grip by the user. The lock ring 482 is substantially similar to the lock rings 282 and 382 described above and includes similar camming surfaces for interfacing with the lock rocker 285.

The lock ring 482 is operated in a similar manner as the lock rings 282 and 382, as described above with respect to FIGS. 28-34. Initially, the resilient tab 484 of the lock ring 482 is pulled out of the first opening 518 of the device coupling assembly 210 and the lock ring 482 is rotated in a clockwise direction. After rotation of the lock ring 482 is completed, the lock rocker 285 is engaged with the drive mechanism 330, namely, the outer gear 338 thereof, as described above. The resilient tab 484 of the lock ring 482 is also reengaged with the device coupling assembly 210 as the feature 490 of the resilient tab 484 engages the second slot 520 of the device coupling assembly 210. The drive coupling assembly 210 is then rotated relative to the drive housing 232 in a clockwise direction to retract/reverse the drive mechanism 330.

Figure 37:
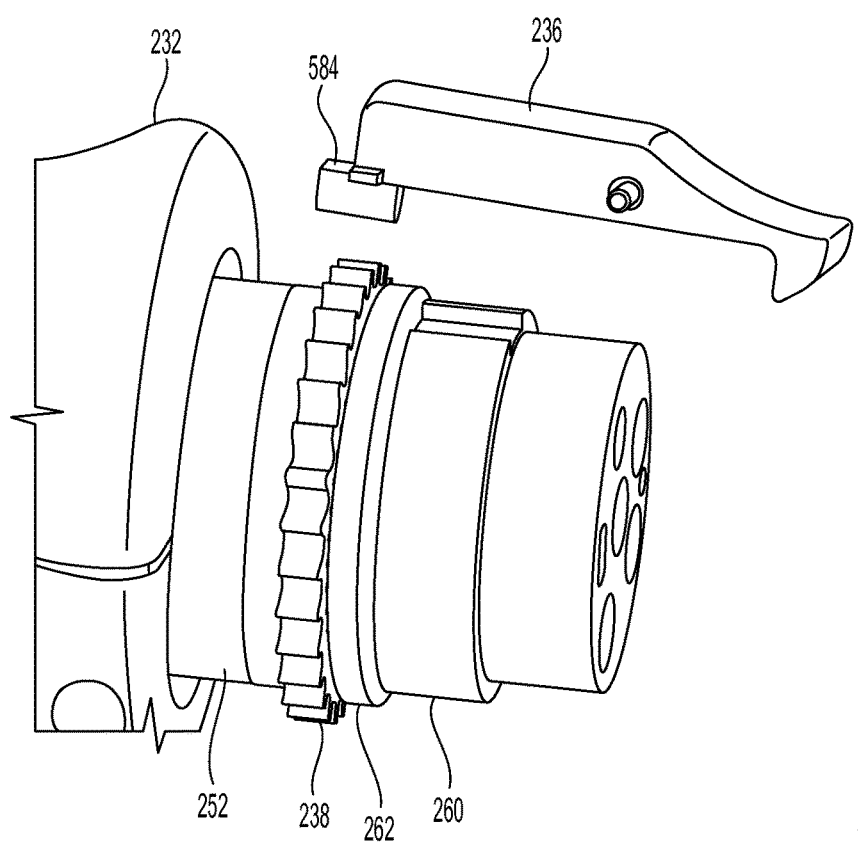
FIG. 37 is a perspective, partially-disassembled view of a drive coupling assembly with a retraction assembly according to another embodiment of the present disclosure.
Figure 38:
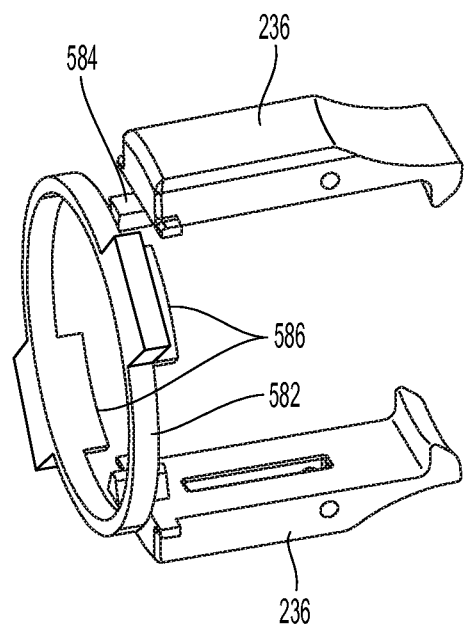
FIG. 38 is a perspective, partially-disassembled view of a lock ring and latches of the refraction assembly of FIG. 37, according to the present disclosure.

FIGS. 37 and 38 show another embodiment of a retraction assembly 580, which is substantially similar to the retraction assembly 280 and only the differences therebetween are described. The retraction assembly 580 includes a lock ring 582 and a tab 584 coupled to a distal end of each of the latches 236. In embodiments, only one of the pair of latches 236 may include the tab 584. The tab 584 is configured and dimensioned to interface with the outer gearing surface 338b of the outer gear 338 (FIG. 37). The lock ring 582 includes a pair of camming tabs 586 configured and dimensioned to interface with the tabs 584 of the latches 236, upon a rotation of lock ring 582 to thereby engage the tabs 584 with the outer gear 338.

During operation, after the instrument 100 is disconnected from the adapter assembly 200, proximal ends of the latches 236 are pressed down or radially inward, thereby pivoting the latches 236 and engaging the tabs 584 with the outer gear 338. The lock ring 582 is then rotated in a clockwise direction to engage the tabs 586 thereof with the tabs 584 of the latches 236 thereby maintaining engagement of the tabs 584 with the outer gear 338. Continual rotation of the lock ring 582 reverses and/or retracts the drive mechanism 330, as described above with respect to FIGS. 28-36.

Figure 39:
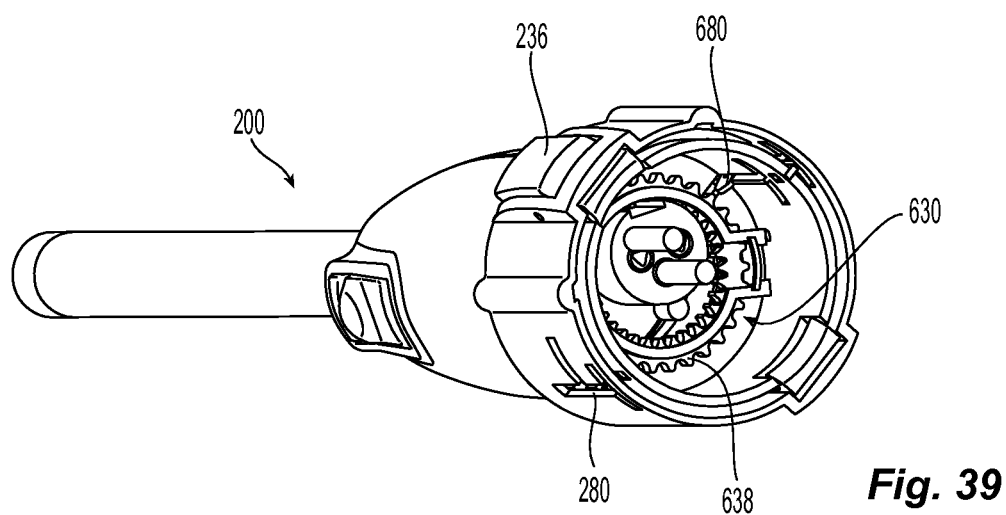
FIG. 39 is a rear, perspective view of the adapter assembly of FIG. 1 with an articulation drive mechanism and an articulation retraction assembly, according to the present disclosure.
Figure 40:
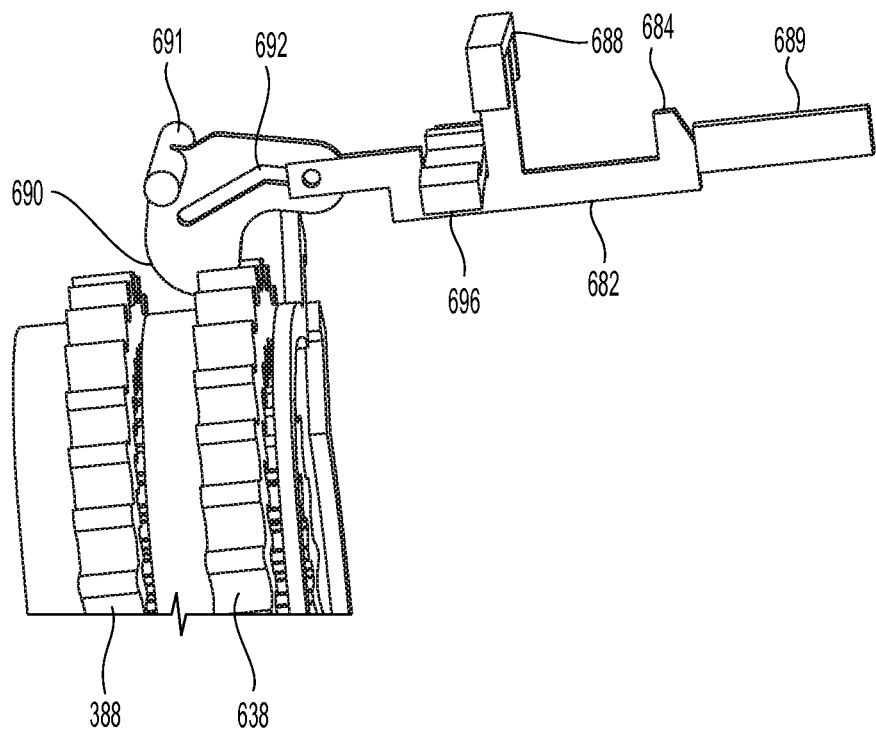
FIG. 40 is a side, partially-disassembled view of the articulation retraction assembly of FIG. 39, according to the present disclosure.
Figure 41:
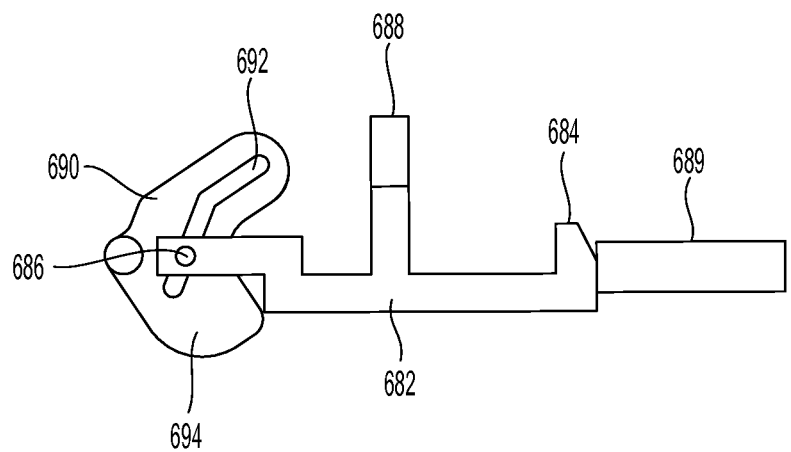
FIG. 41 is a side view of a slidable button and a cam lock of the articulation retraction assembly of FIG. 39, according to the present disclosure.

FIGS. 39-47 illustrate a second retraction assembly 680 for retracting and/or reversing an articulation mechanism 630 of the drive mechanism 330. With reference to FIGS. 39 and 40, the articulation mechanism 630 is configured to articulate the tool assembly 304 of end effector 300 about an articulation axis that is transverse to longitudinal axis "X-X" (FIG. 1). The articulation mechanism 630 includes an articulation drive shaft (not shown) having a keyed distal end dimensioned and configured to engage the connector sleeve 220 such that rotation thereof is transferred to the articulation drive shaft. The articulation drive shaft also includes a spur gear (not shown) meshingly engaged with an idler gear (not shown). The drive mechanism 630 further includes an outer gear 638 (FIGS. 39 and 40). The idler gear is rotationally disposed over one of the shafts 256 and acts as a planetary gear interconnecting the spur gear with the outer gear 638 thereby allowing for transfer of rotational motion from the spur gear to the outer gear 638. The outer gear 638 is freely rotatable unless engaged by the retraction assembly 680 as described in further below.

With reference to FIGS. 40-43, the retraction assembly 680 includes a slidable button 682 disposed within a slot 211 of the drive coupling assembly 210. The slidable button 682 includes a proximally-facing latch 684 for engaging the drive coupling assembly 210 when the slidable button 682 is pulled in a proximal direction. The slidable button 682 also includes a pin 686 at a distal end thereof for interfacing with a cam lock 690, as described in further detail below, and a grip feature 688 extending upwardly through the drive coupling assembly 210 allowing for better grip by the user. The slidable button 684 may further include an extension 689 disposed at the proximal end thereof to facilitate in the rotation of the drive coupling assembly 210 when the slidable button 684 is extended proximally.

The retraction assembly 680 also includes the cam lock 690 having a cam slot 692 therein for engaging the pin 686 of the slidable button 682. The cam lock 690 is pivotally coupled to the drive coupling assembly 210 via a pivot pin 691. The cam lock 690 also includes a feature 694 for engaging the outer gear 638 of the articulation mechanism 630. In operation, as slidable button 684 is pulled in the proximal direction, the pin 686 travels through the cam slot 692 of the cam lock 690, pushing the cam lock 690 in a distal and downward (radially inward) direction thereby engaging the feature 694 of the cam lock 690 with the outer gear 638.

The retraction assembly 680 also includes a spring-loaded release switch 696, which controls longitudinal movement of the slidable button 682. The release switch 696 moves along an axis transverse to the axis "X-X" (FIG. 1) and prevents movement of grip feature 688 unless the release switch 696 is drawn back. When the slidable button 682 is in its so-called "home" (e.g., proximal) configuration and the cam lock 690 is disengaged from the articulation mechanism 630, the release switch 696 is disposed proximally of the grip feature 688. When the slidable button 682 is in its distal configuration and the cam lock 690 is engaged with the articulation mechanism 630, the release switch 696 is disposed distally of the grip feature 688. Thus, to transition from proximal or distal configurations, the release switch 696 is drawn back prior to movement of the grip feature 688 to either engage or disengage the retraction assembly 680 with the articulation mechanism 630.

Figure 42:
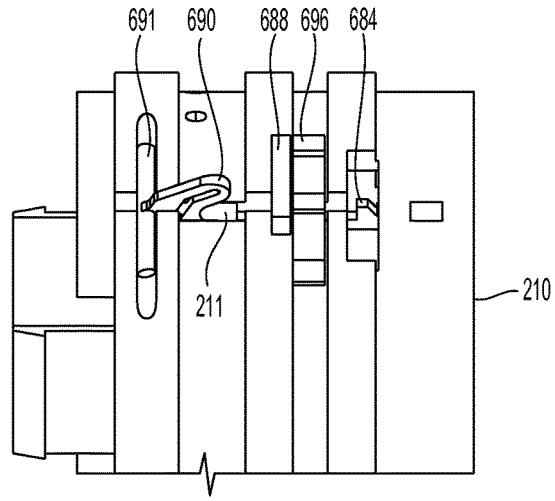
FIG. 42 is a side view of the adapter assembly of FIG. 1 with the articulation retraction assembly of FIG. 39 in a home configuration, according to the present disclosure.
Figure 43:
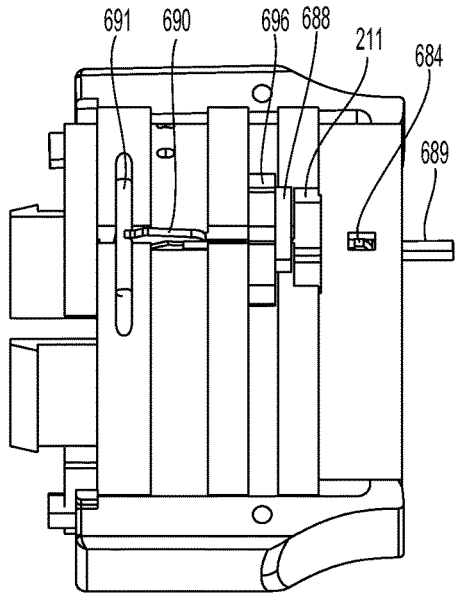
FIG. 43 is a side view of the adapter assembly of FIG. 1 with the articulation retraction assembly of FIG. 39 engaged with the articulation drive mechanism, according to the present disclosure.
Figure 44:
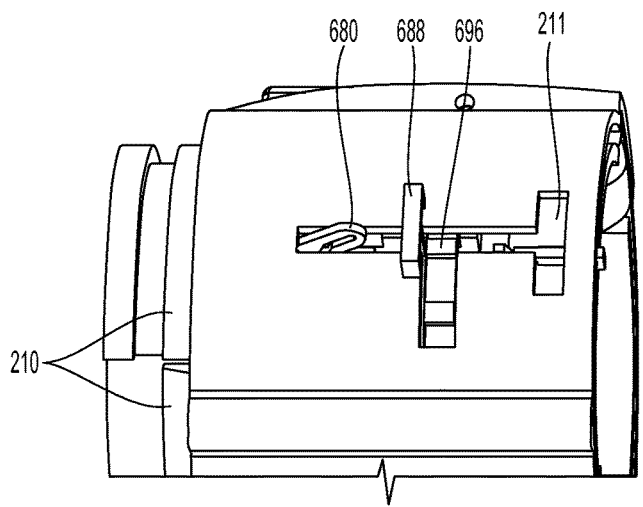
FIG. 44 is a side view of the adapter assembly of FIG. 1 with the articulation retraction assembly of FIG. 39 in a home configuration and a release switch in a closed configuration, according to the present disclosure.
Figure 45:
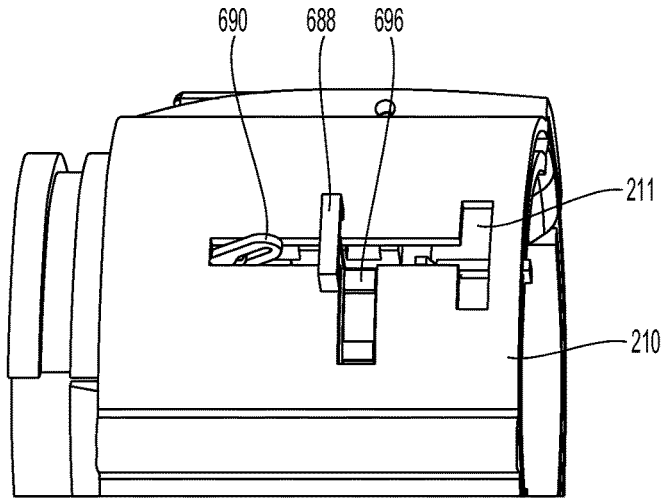
FIG. 45 is a side view of the adapter assembly of FIG. 1 with a release switch in an open configuration and the slidable button in a distal configuration, according to the present disclosure.
Figure 46:
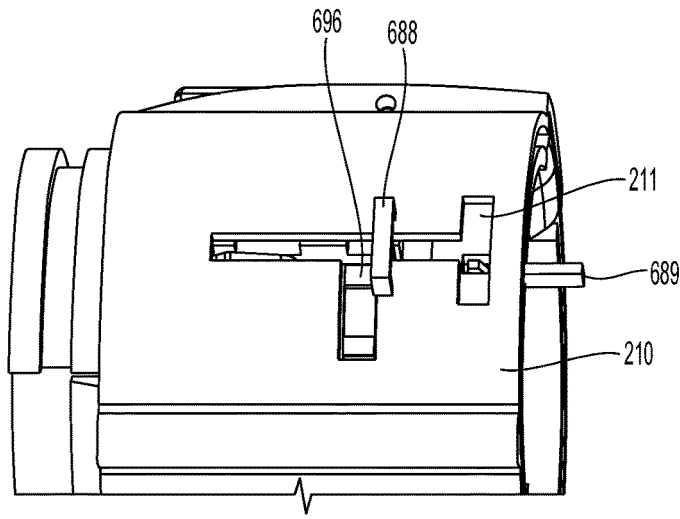
FIG. 46 is a side view of the adapter assembly of FIG. 1 with a release switch in the open configuration and the slidable button in a proximal configuration, according to the present disclosure.
Figure 47:
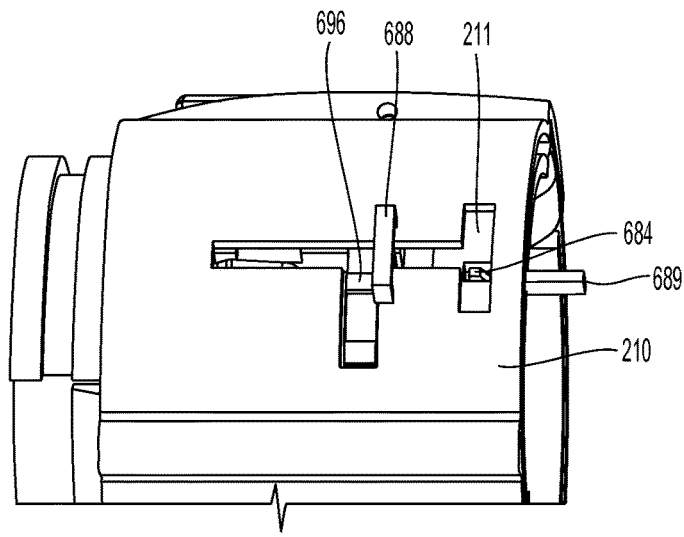
FIG. 47 is a side view of the adapter assembly of FIG. 1 with a release switch in the closed configuration and the slidable button in the proximal configuration, according to the present disclosure.

With reference to FIGS. 44-47, operation of the refraction assembly 680 is described. During use, when manual retraction of the articulation mechanism 630 is desired or required, the adapter assembly 200 is disconnected from the surgical instrument 100. Thereafter the retraction assembly 680 is engaged with the articulation mechanism 630. As shown in FIGS. 42 and 44, initially the retraction assembly 680 is in its so-called "home" configuration in which the slidable button 682 is in its distal configuration and the cam lock 690 is not engaged with the outer gear 638 of the articulation mechanism 680. As shown in FIGS. 45 and 46, the release switch 696 is pulled or slid across the slot 211 of the drive coupling assembly 210 allowing the slidable button 682 to be pulled proximally. As the slidable button 682 is pulled or slid back, the proximally-facing latch 684 engages the drive coupling assembly 210, maintaining the slidable button 682 in the proximal position. The cam lock 690 also engages the outer gear 638 of the articulation mechanism 680, as described above, and the release switch 696 is slid back into place, preventing distal movement of the slidable button 682.

Figure 48:
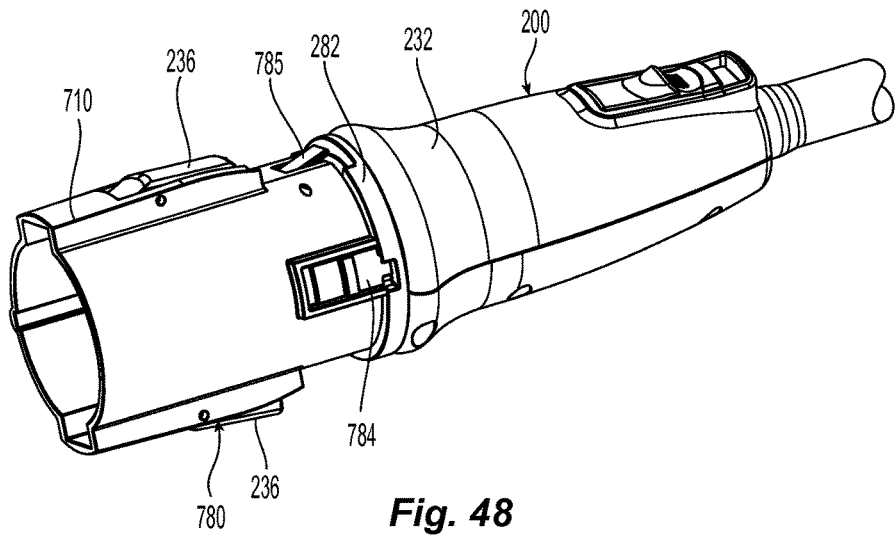
FIG. 48 is a perspective view of an adapter assembly with a retraction assembly according to another embodiment of the present disclosure.

FIGS. 48-55 illustrate another embodiment of a retraction assembly 780, which is substantially similar to the retraction assembly 280 and only the differences therebetween are described. The retraction assembly 780 includes the lock ring 282, which is unchanged, a spring-loaded lock bolt 784, and a lock rocker 785. The refraction assembly 780 is disposed within a drive coupling assembly 710, which is substantially similar to the drive coupling assembly 210. The drive coupling assembly 710 may be longer than the drive coupling assembly 210 to accommodate the lock rocker 785, as shown in FIG. 48.

Figure 49:
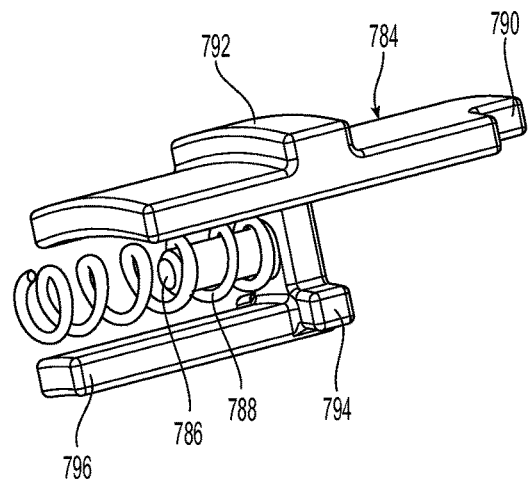
FIG. 49 is a perspective view of a lock bolt according to another embodiment of the present disclosure.

With reference to FIG. 49, the lock bolt 784 includes a proximally-facing post 786 having a spring 788 disposed thereon, which biases the lock bolt 784 in a distal direction (e.g., toward the lock ring 282). The lock bolt 784 also includes a feature 790 for interfacing with the lock ring 282 as described in further detail below and a grip feature 792 allowing for better grip by the user. The lock bolt 784 further includes opposing, laterally-facing tabs 794 for slidably coupling of the lock bolt 784 to the drive coupling assembly 710. The lock bolt 784 also includes a proximally facing stop member 796 configured to prevent coupling of the adapter assembly 200 to the surgical device 100, if the retraction assembly 780 has been engaged, as described in further detail below.

Figure 50:
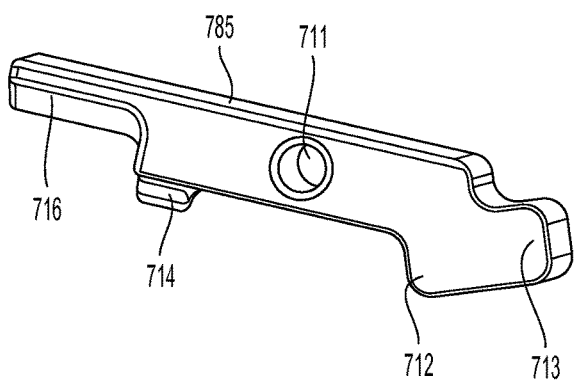
FIG. 50 is a perspective view of a lock rocker according to another embodiment of the present disclosure.
Figure 52:
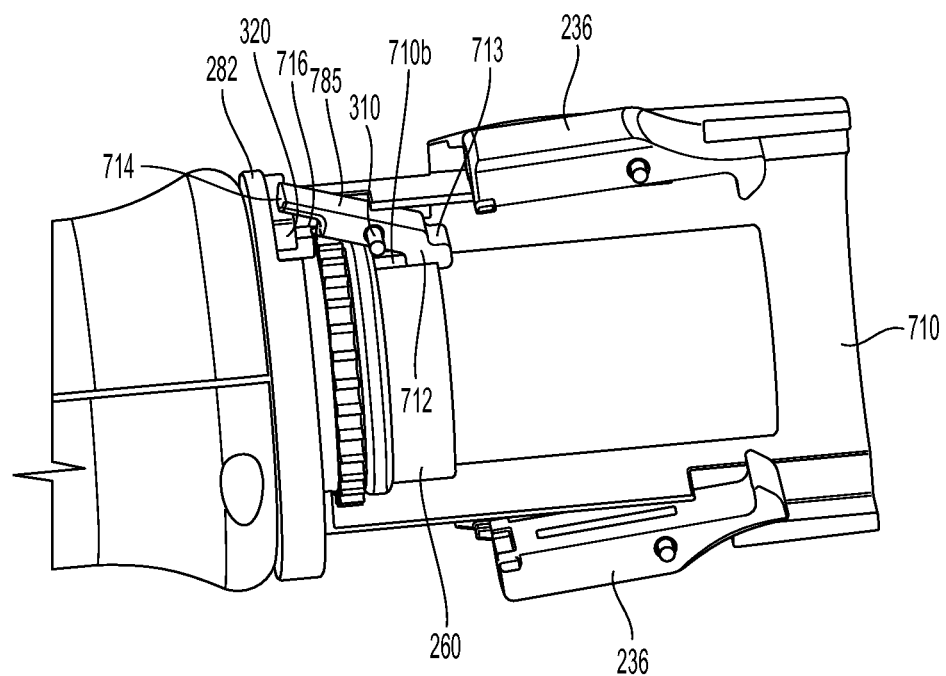
FIG. 52 is a perspective, partially-disassembled view of the retraction assembly of FIG. 48 in its home configuration with the lock rocker of FIG. 50 disengaged from an outer gear, according to the present disclosure.
Figure 55:
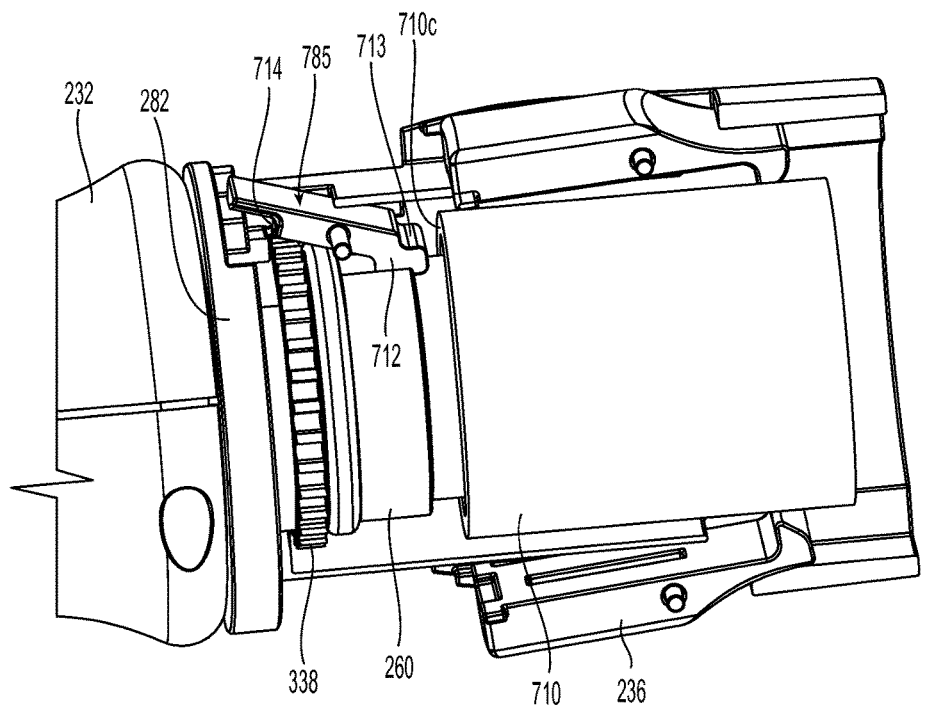
FIG. 55 is a perspective, partially-disassembled view of the retraction assembly of FIG. 48 with the lock ring fully rotated and pivoting the lock rocker, according to the present disclosure.
Figure 56:
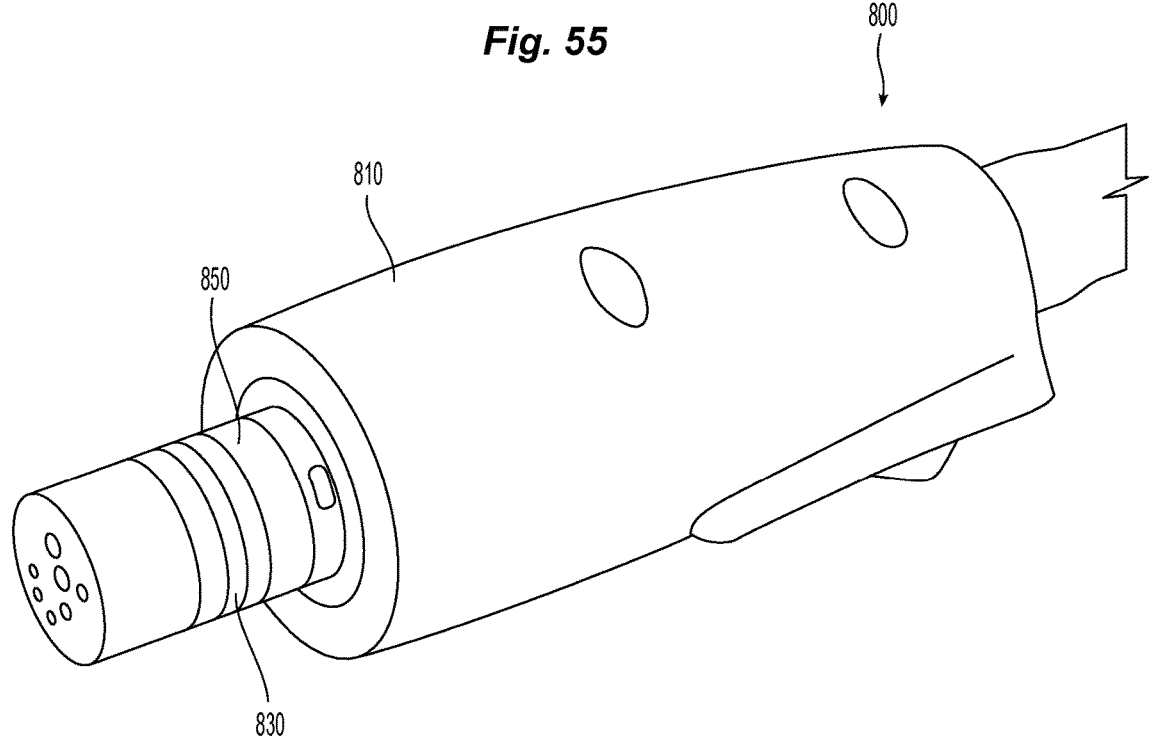
FIG. 56 is a perspective view of an adapter assembly with a retraction assembly according to yet another embodiment of the present disclosure.

With reference to FIG. 50, the lock rocker 785 is pivotally supported on pivot pin 310 (FIG. 52) that is disposed within an opening 711 of lock rocker 785 to pivotally couple the lock rocker 785 to the drive coupling assembly 710, wherein the pivot pin 310 is disposed at a location distal of one of the latches 236. As shown in FIGS. 17 and 52, the lock rocker 785 includes a latching feature 712 disposed at a proximal end thereof, a tooth feature 714 disposed distally of the pivot pin 310, and a camming feature 716 disposed at a distal end thereof. As shown in FIG. 55, the latching feature 712 is configured to engage a slot 260a disposed on the distal housing block 260. The tooth feature 714 of the lock rocker 785 is configured to engage the outer gear 338 and the camming feature 716 of the lock rocker 785 is configured to engage the lock ring 282. The lock rocker 785 also includes a proximally facing stop member 713 configured to prevent coupling of the adapter assembly 200 to the surgical device 100, if the retraction assembly 780 has been engaged by the lock rocker 785 as described in further detail below.

Figure 51:
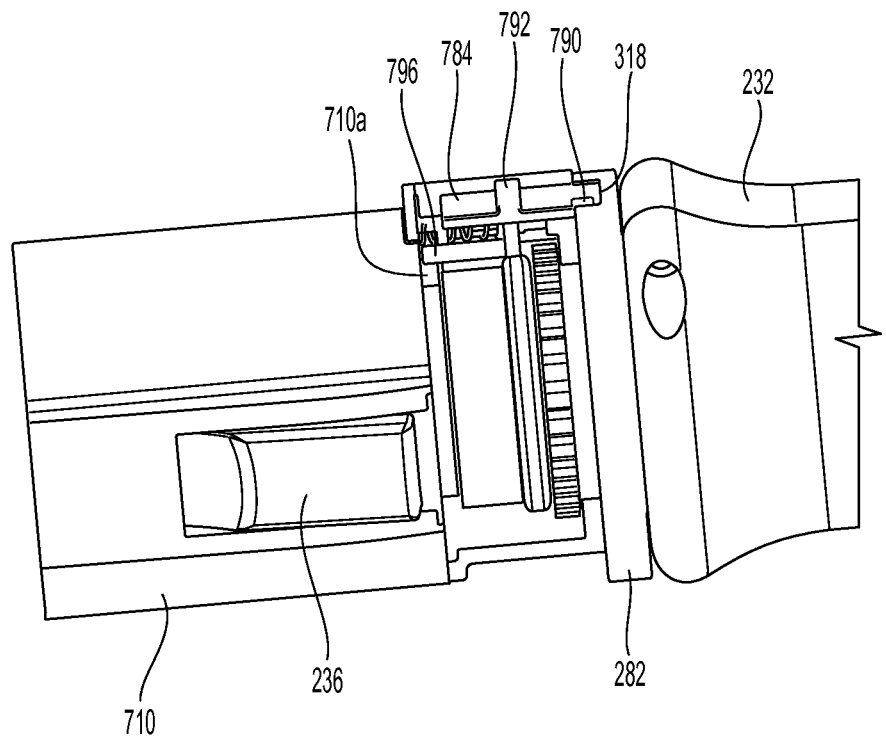
FIG. 51 is a perspective, partially-disassembled view of the retraction assembly of FIG. 48 in its home configuration with the lock bolt of FIG. 49 engaged with a lock ring, according to the present disclosure.

The retraction assembly 780 is operated in a similar manner as the retraction assembly 280, as described above with respect to FIGS. 28-31. FIGS. 48, 51, and 52 show the retraction assembly 780 in its so-called "home" configuration, in which the lock ring 282 is disengaged from the drive mechanism 330. As shown in FIG. 51, in the "home" configuration, the lock bolt 784 is biased by the spring 788 to engage the lock ring 282 at the slot 318, thereby preventing rotation of the lock ring 782. As shown in FIGS. 17, 25, and 28, the lock rocker 785 is engaged with the slot 260a of the distal housing block 260 with respect to the lock rocker 285. In the "home" configuration, the lock rocker 785, and in particular the camming feature 716 of the lock rocker 785 is initially engaged with the first camming surface 320 of the lock ring 282. Further, in the "home" configuration, the stop members 796 and 713 of the lock bolt 784 and the lock rocker 785, respectively, align with respective slots 710a and 710b defined in the connecting portion 108, allowing for coupling of the adapter assembly 200 to the surgical device 100.

Figure 53:
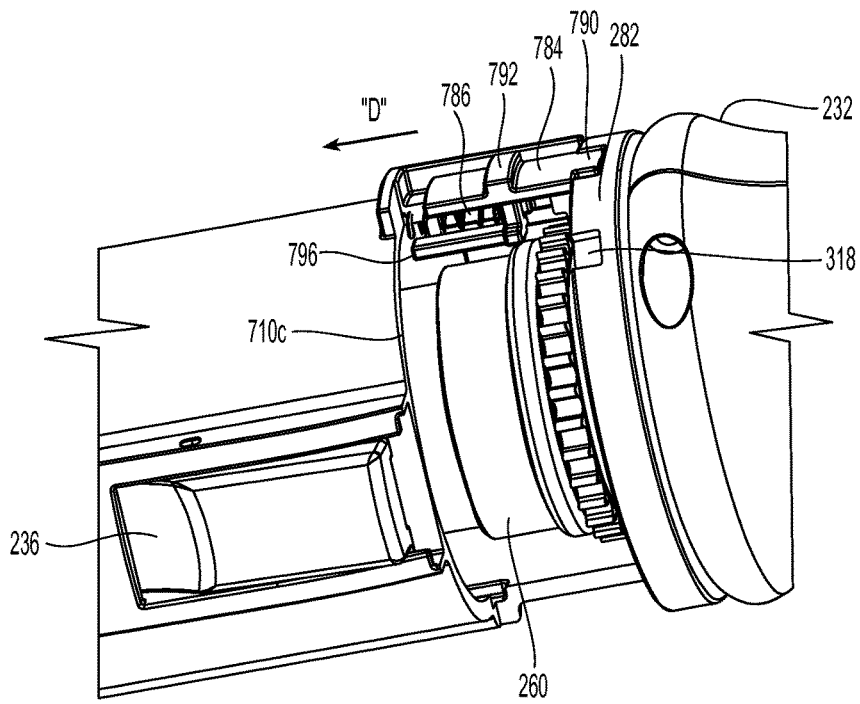
FIG. 53 is a perspective, partially-disassembled view of the retraction assembly of FIG. 48 with the lock bolt disengaged from the lock ring that is partially rotated, according to the present disclosure.
Figure 54:
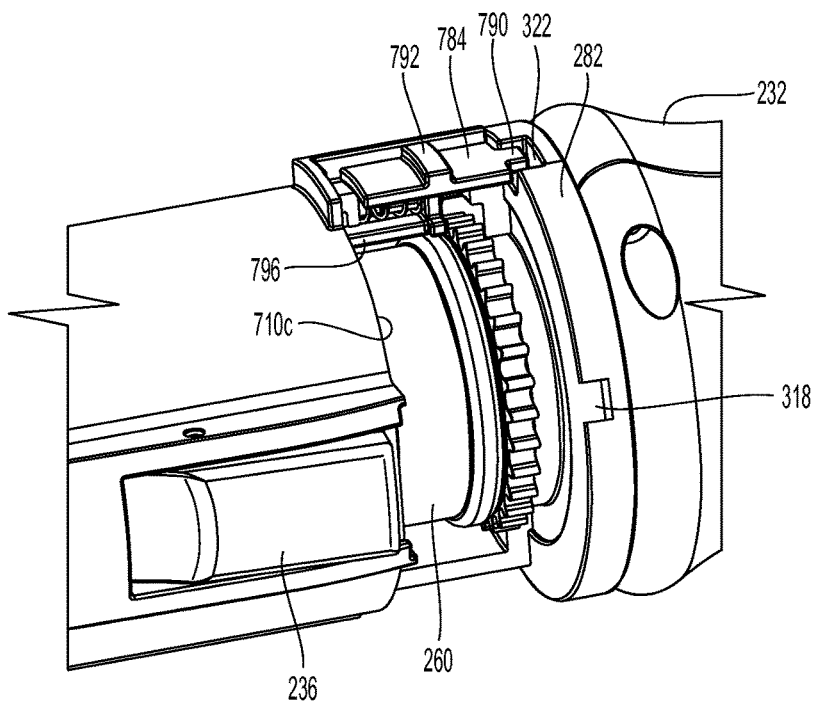
FIG. 54 is a perspective, partially-disassembled view of the retraction assembly of FIG. 48 with the lock bolt engaged with the lock ring that is fully rotated, according to the present disclosure.

FIG. 53 shows the lock bolt 784 being disengaged from the lock ring 282 by pulling the lock bolt 784 in a proximal direction, as indicated by arrow "D," thus allowing for rotation of the lock ring 282 in a clockwise direction to begin the refraction process. As the lock ring 282 is initially rotated, the camming feature 716 of the lock rocker 785 is still engaged with the first camming surface 320 of the lock ring 282 but travels along the first camming surface 320 and contacts the first camming portion 324a of the second camming surface 320, as described above with respect to the lock rocker 285. As the rotation of the lock ring 282 is continued, the camming feature 716 of the lock rocker 785 continues to travel along the second camming portion 324b of the second camming surface 320. Further, as the rotation of the lock ring 282 as shown in FIG. 54, the lock bolt 784 is also reengaged with the lock ring 282 by the spring 788 and rests against the abutment surface 322. FIG. 55 also shows completed rotation of the lock ring 782 in which the drive coupling assembly 710 is engaged with the drive mechanism 330, namely, via the lock rocker 785 to the outer gear 338.

After the drive coupling assembly 710 is in its retracted configuration, in which it is engaged to the drive mechanism 330, the drive coupling assembly 710 is rotated relative to the drive housing 232 in a clockwise direction along with the lock ring 282, the outer gear 338 is also rotated via the lock rocker 285. This, in turn, rotates the drive shaft 332 via the idler gear 334 and reverses and/or retracts the anvil assembly 306 relative to cartridge assembly 308 of end effector 300.

Once the drive coupling assembly 710 is in its retracted configuration, the stop member 713 of the lock rocker 785 and the stop member 796 of the lock bolt 784 are aligned within the drive coupling assembly 710, such that they abut distal end 710c of the connecting portion 108, preventing coupling of the surgical device 100 to the adapter assembly 200.

Figure 57:
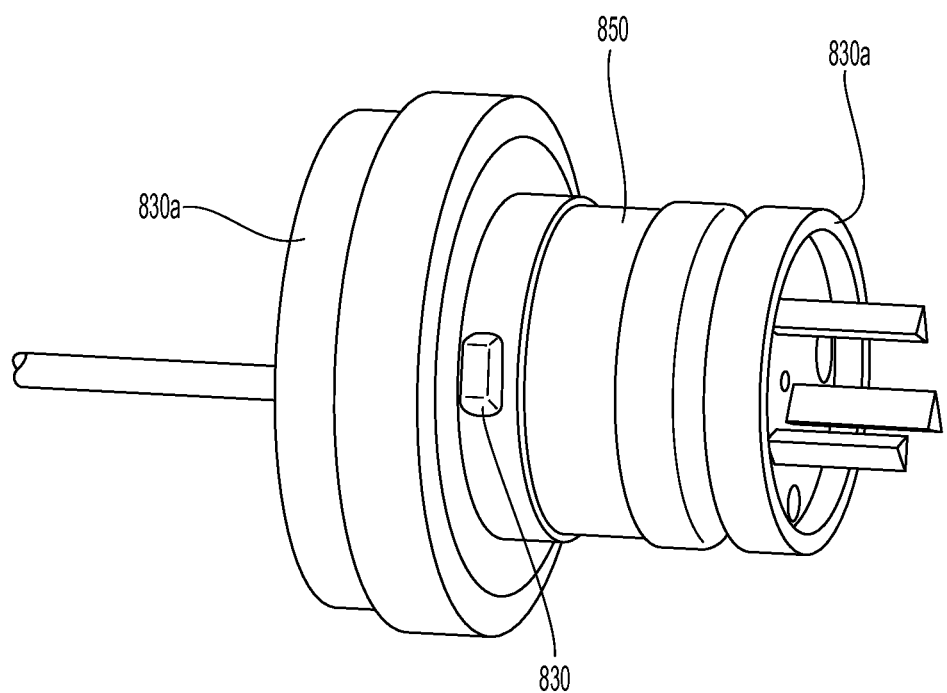
FIG. 57 is a side, partially-disassembled view of a drive mechanism and the retraction assembly of the adapter assembly of FIG. 56, according to the present disclosure.

With reference to FIGS. 56-61, another embodiment of an adapter assembly 800 is shown. The adapter assembly 800 does not include the drive coupling 210, but is otherwise substantially similar to the adapter assembly 200. As shown in FIG. 57, the adapter assembly 800 includes a drive mechanism 830 for actuating, rotating, and articulating the end effector 300 and a retraction assembly 850 for retracting the drive mechanism 830. The drive mechanism 830 includes a proximal housing 830a and a distal housing 830b including a plurality of drive shafts (e.g., drive shaft 832).

Figure 58:
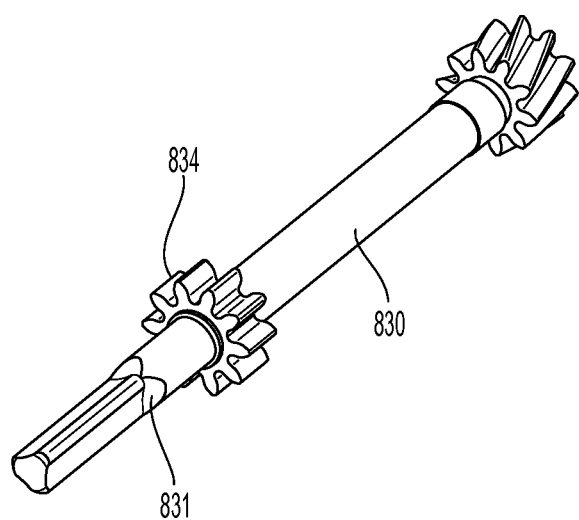
FIG. 58 is a perspective view of a drive shaft of the drive mechanism of FIG. 57 according to the present disclosure.
Figure 59:
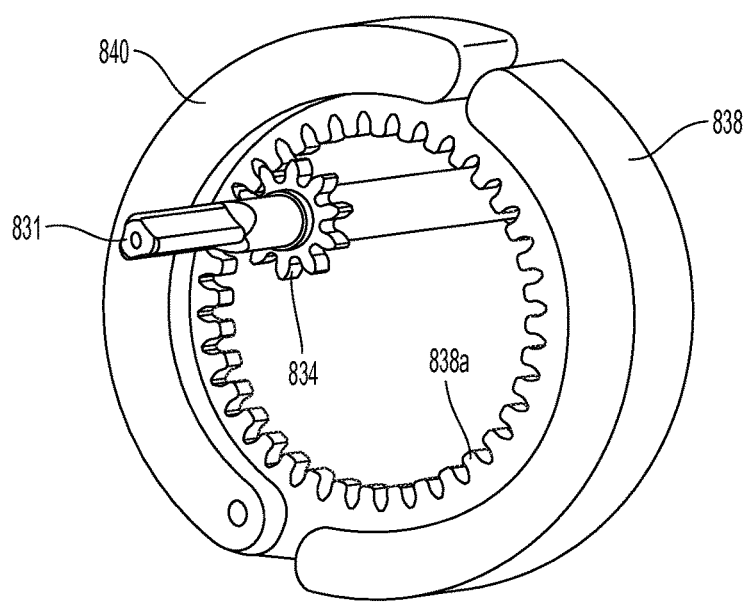
FIG. 59 is a perspective view illustrating a gear supported on the drive shaft of FIG. 58 meshingly engaged with a retraction gear according to the present disclosure.

With reference to FIGS. 58 and 59, the drive mechanism 830 includes a drive shaft 832 having a keyed distal end 831 dimensioned and configured to engage the connector sleeve 218 such that rotation thereof is transferred to the drive shaft 832. The drive shaft 832 also includes a spur gear 834 meshingly engaged with an inner geared surface 838a of a retraction gear 838 of the retraction assembly 850. The retraction gear 838 is freely rotatable by the drive shaft 832 via the spur gear 834 while the surgical device 100 rotates the drive shaft 832. During retraction, when the adapter assembly 800 is disconnected from the surgical device 100, rotation of the retraction gear 838 rotates the drive shaft 832 thereby retracting and/or reversing the drive mechanism 830.

Figure 60:
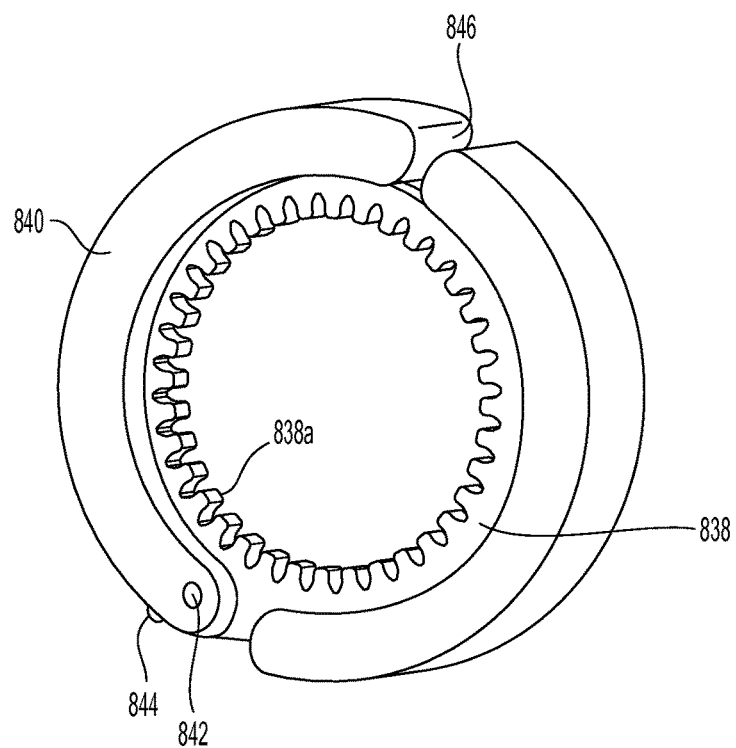
FIG. 60 is a perspective view of the retraction gear of FIG. 59 in a closed configuration according to the present disclosure.
Figure 61:
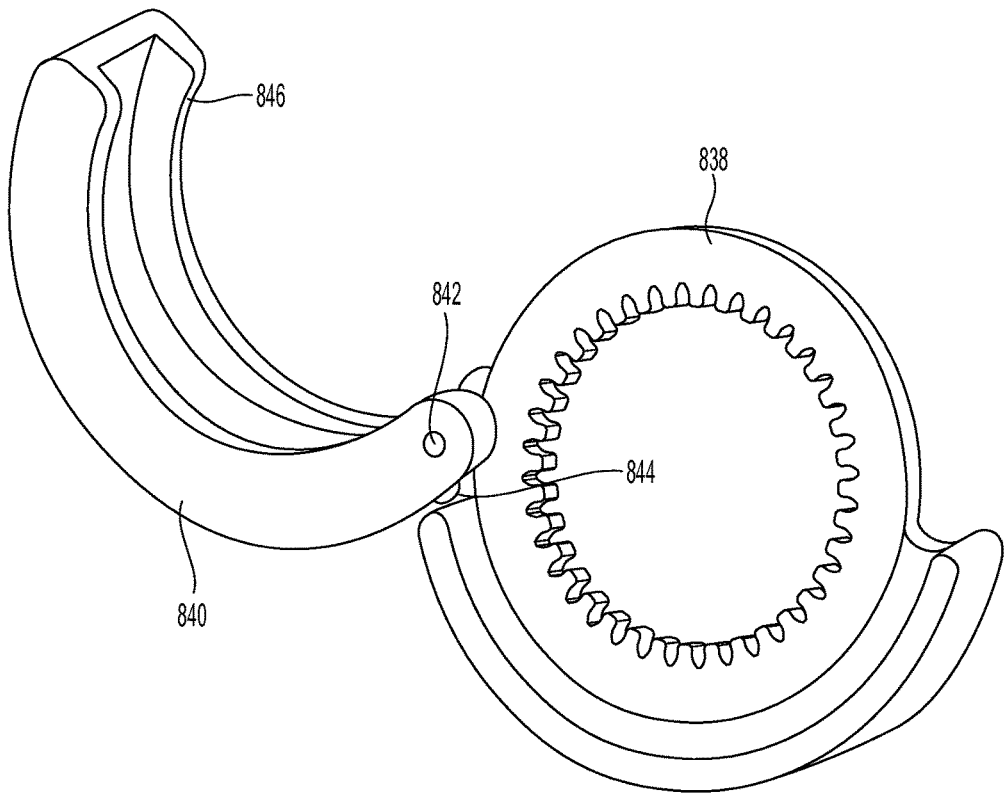
FIG. 61 is a perspective view of the retraction gear of FIG. 59 in an open configuration according to the present disclosure.

With reference to FIGS. 60 and 61, the retraction gear 838 includes a latch 840 pivotally coupled thereto at a pivot 842. The latch 840 has a substantially arcuate shape, such that when the latch 840 is in its closed configuration relative to the retraction gear 838, a ring is formed as shown in FIG. 60. The latch 840 includes a stop feature 844 at its pivot 842 to limit pivoting of the latch 840 relative to the retraction gear 838. As shown in FIG. 61, the latch 840 also includes a grip feature 846 at the opposite of end of the pivot 842 allowing the user to grasp the latch 840 and pivot the latch 840 into its pivot configuration.

As shown in FIG. 61, during operation, after the adapter assembly 800 is disconnected from the instrument 100, the latch 840 is pivoted into an open configuration in which the latch 840 extends radially from the retraction gear 838. Thereafter, the user grasps the retraction gear 838 by the latch 840 and rotates the retraction gear 838 in a desired (e.g., clockwise) direction. Continual rotation of the retraction gear 838 reverses and/or retracts the drive mechanism 330 as described above.

Figure 62:
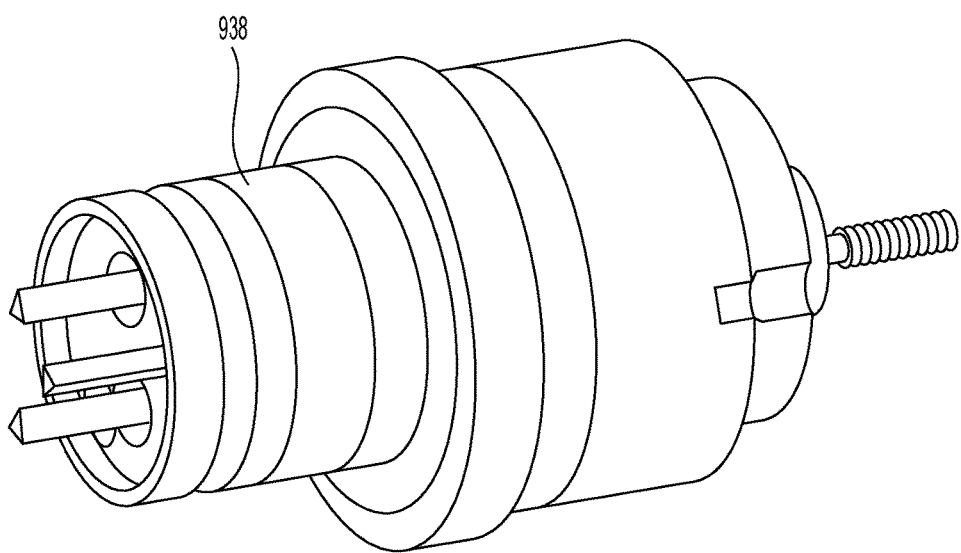
FIG. 62 is a perspective, partially-disassembled view of the drive mechanism of FIG. 57 and a retraction assembly according to another embodiment of the present disclosure.
Figure 63:
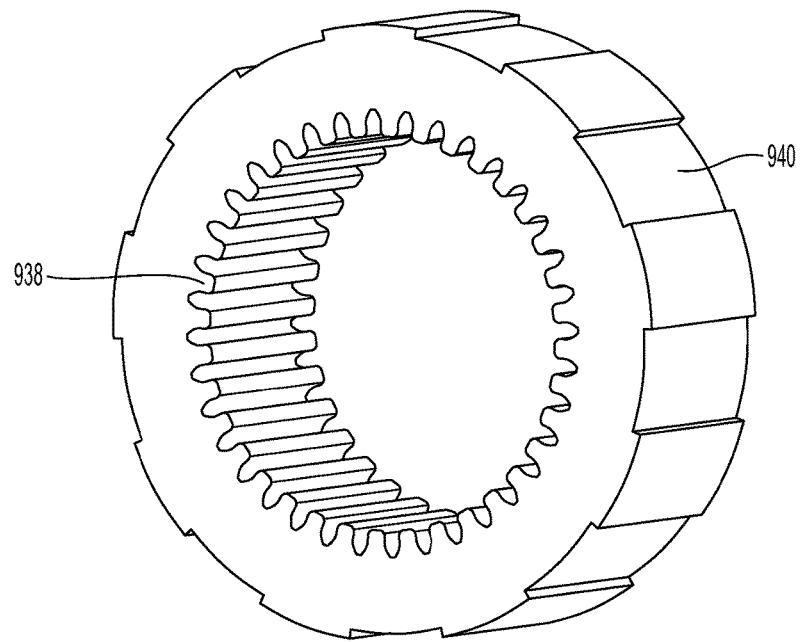
FIG. 63 is a perspective view of a refraction gear according to another embodiment of the present disclosure.

With reference to FIGS. 62 and 63 another embodiment of the retraction gear 938 is illustrated. The retraction gear 938 includes an outer textured surface 940 that may be gripped by the user during retraction. The retraction gear 938 is operated in the same manner as the retraction gear 838 as described above. In embodiments, the retraction gear 938 may include both the outer textured surface 940 and the latch 840.

Figure 64:
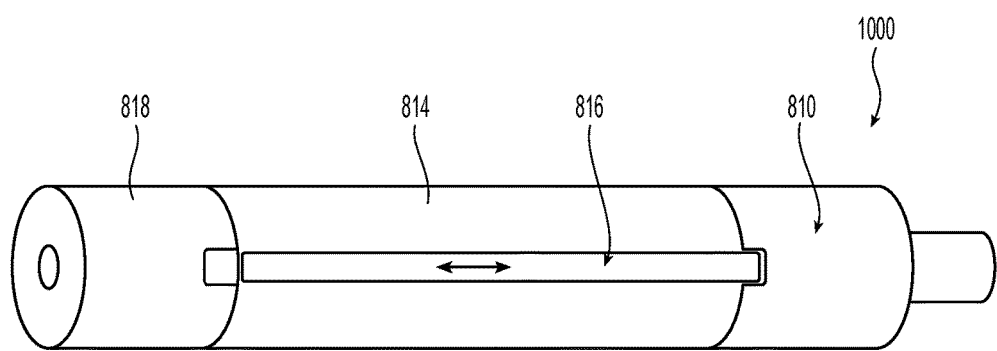
FIG. 64 is a schematic, perspective view of an adapter assembly having a retraction assembly according to another embodiment of the present disclosure.

With reference to FIGS. 59 and 64, another embodiment of a retraction gear 1000 of the adapter assembly 800 is shown. The adapter assembly 800 includes a proximal housing 810 enclosing a thrust bearing housing 812 coupled thereto. The adapter assembly 800 also includes a ported inner tube 814, which encloses drive linkages and rods (not shown) of the adapter assembly 800. The adapter assembly 800 also includes a longitudinally slidable beam 816 movable from a proximal position to a distal position. In the proximal position, the slidable beam 816 radially-orients the thrust bearing housing 812 to the ported inner tube 814 thereby maintaining the thrust bearing housing 812 and the inner tube 814 in a radially-locked configuration. In the distal position, the slidable beam 816 is engaged to a tip housing 818 allowing for retraction of the drive mechanism 830 as described below.

During normal operation, namely, when the adapter assembly 800 is coupled to the surgical device 100 and the adapter assembly 800 is transmitting rotational forces to the end effector 300, the slidable beam 816 is in the proximal configuration. This forces the inner tube 814 to rotate with the thrust bearing housing 812 when the adapter assembly 800 is rotated. In particular, during rotation, when the drive shaft 832 is rotated, the thrust bearing housing 812 is also rotated along with the inner tube 814, such that no firing and/or actuation of the end effector 300 occurs.

During retraction, namely, when retraction of the adapter assembly 200 is initiated, the slidable beam 816 is moved into the distal configuration by the user. This disengages the inner tube 814 from the thrust bearing housing 812 and engages the inner tuber 812 with a tip housing 818. Rotation of the adapter assembly 800 causes the thrust bearing housing 812, which is coupled thereto via the proximal housing 810, to rotate along with the drive shaft 832 without rotation of the inner tube 814. Continual rotation of the adapter assembly 800 reverses and/or retracts the drive mechanism 830 since rotation of the adapter assembly 800 rotates the thrust bearing housing 812, which in turn, rotates the drive shaft 832 thereby retracting and/or reversing the drive mechanism 830.

It will be understood that various modifications may be made to the embodiments disclosed herein. For example, the instrument 100 need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as limiting, but merely as exemplifications of preferred embodiments. Those skilled in the art will envision other modifications within the scope and spirit of the claims appended thereto.

The invention claimed is:

1. A surgical device adapter for coupling an end effector of a surgical device to a handle assembly, the surgical device adapter comprising:
   a housing;
   a drive mechanism disposed within the housing and couplable to the handle assembly and the end effector; and
   a drive coupling assembly selectively couplable to the handle assembly, the drive coupling assembly including:
      a retraction assembly movable from a first configuration to a second configuration, the retraction assembly including:
         a lock rocker pivotally coupled within the drive coupling assembly; and
         a lock ring rotatable about the longitudinal axis and relative to the drive coupling assembly, wherein upon rotation thereof the lock ring is configured to actuate the lock rocker to engage with the drive mechanism; and
      a latch pivotally coupled to the retraction assembly and configured to engage the handle assembly,
      wherein in the first configuration the retraction assembly is disengaged from the drive mechanism and in the second configuration the retraction assembly is engaged with the drive mechanism.

2. The surgical device adapter according to claim 1, wherein the drive coupling assembly is configured to rotate about a longitudinal axis defined by the surgical device adapter and relative to the housing such that when the retraction assembly is in the second configuration, rotation of the drive coupling assembly actuates the drive mechanism.

3. The surgical device adapter according to claim 1, wherein the lock rocker further comprises a first proximally facing stop member configured to abut the surgical device to prevent coupling thereof to the handle assembly when the retraction assembly is in the second configuration.

4. The surgical device adapter according to claim 1, wherein the retraction assembly further comprises:
   a spring-loaded lock bolt slidably coupled to the drive coupling and engaged with the lock ring, the lock bolt configured to prevent rotation of the lock ring.

5. The surgical device adapter according to claim 4, wherein the lock bolt further comprises a second proximally facing stop member configured to abut the surgical device to prevent coupling thereof to the handle assembly when the retraction assembly is in the second configuration.

6. A surgical device adapter for coupling an end effector to a handle assembly, the surgical device adapter comprising:
   a housing;
   a drive mechanism disposed within the housing and couplable to the handle assembly and the end effector; and
   a retraction assembly rotationally coupled to the drive mechanism, the retraction assembly including:
      a retraction gear including:
         an inner geared surface mechanically engaged with the retraction gear; and
         a latch pivotally coupled to the retraction assembly about a pivot, and being movable from a closed configuration in which the latch is disposed about the retraction gear and an open configuration in which the latch radially extends from the retraction gear, and
      wherein the retraction assembly is configured to rotate about a longitudinal axis defined by the surgical device adapter in response to rotation of the drive mechanism, and to rotate the drive mechanism.

7. The surgical device adapter according to claim 6, wherein the drive mechanism comprises:
   a drive shaft coupled to the end effector and configured to actuate the first and second jaws, the drive shaft non-rotatably supporting a gear.

8. The surgical device adapter according to claim 6, wherein the latch includes a stop feature disposed adjacent the pivot to limit pivoting of the latch relative to the retraction gear.

9. The surgical device adapter according to claim 6, wherein the retraction gear comprises a grip surface along at least a portion of an outer surface thereof.

10. A surgical device comprising:
    an end effector including a first jaw and a second jaw moveable relative to the first jaw;
    a handle assembly including at least one motor mechanically coupled to the jaw assembly; and an adapter assembly removably coupled to a proximal end of the jaw assembly and a distal end of the handle assembly, the adapter assembly comprising:

a housing;

a drive mechanism disposed within the housing and configured to couple the at least one motor to the end effector; and a drive coupling assembly selectively couplable to the handle assembly, the drive coupling assembly including:

a retraction assembly movable from a first configuration to a second configuration, the retraction assembly including:

a lock rocker pivotally coupled within the drive coupling assembly; and a lock ring rotatable about the longitudinal axis and relative to the drive coupling assembly, wherein upon rotation thereof the lock ring is configured to actuate the lock rocker to engage with the drive mechanism; and a latch pivotally coupled to the retraction assembly and configured to engage the handle assembly, wherein in the first configuration the retraction assembly is disengaged from the drive mechanism and in the second configuration the retraction assembly is engaged with the drive mechanism and prevents coupling of the handle assembly to the adapter assembly device.

11. The surgical device according to claim 10, wherein the drive coupling assembly is configured to rotate about a longitudinal axis defined by the adapter assembly device and relative to the housing such that when the retraction assembly is in the second configuration rotation of the drive coupling assembly actuates the drive mechanism.

12. The surgical device according to claim 10, wherein the lock rocker of the retraction assembly comprises a first proximally facing stop member configured to abut the surgical device to prevent coupling of the adapter assembly to the handle assembly when the retraction assembly is in the second configuration.

13. The surgical device according to claim 10, wherein the retraction assembly further comprises:

a spring-loaded lock bolt slidably coupled to the drive coupling and engaged with the lock ring, the lock bolt configured to prevent rotation of the lock ring.

14. The surgical device according to claim 13, wherein the lock bolt of the retraction assembly comprises a second proximally facing stop member configured to abut the surgical device to prevent coupling of the adapter assembly to the handle assembly when the retraction assembly is in the second configuration.

* * * * *